US006730883B2

(12) United States Patent
Brown et al.

(10) Patent No.: US 6,730,883 B2
(45) Date of Patent: May 4, 2004

(54) FLEXIBLE HEATING COVER ASSEMBLY FOR THERMAL CYCLING OF SAMPLES OF BIOLOGICAL MATERIAL

(75) Inventors: Larry R. Brown, Carlsbad, CA (US); William D. Brumley, Vista, CA (US); Kenneth J. Zajac, San Diego, CA (US)

(73) Assignee: Stratagene, La Jolla, CA (US)

( * ) Notice: Subject to any disclaimer, the term of this patent is extended or adjusted under 35 U.S.C. 154(b) by 0 days.

(21) Appl. No.: 10/262,994

(22) Filed: Oct. 2, 2002

(65) Prior Publication Data

US 2004/0065655 A1 Apr. 8, 2004

(51) Int. Cl.[7] .......................... C12M 1/00; C12M 1/38; H05B 3/20; H05B 3/34; G05D 23/20

(52) U.S. Cl. ...................... 219/428; 219/385; 219/521; 219/530; 219/535; 219/549; 435/286.1; 435/288.4; 435/304.4

(58) Field of Search ................................ 219/385, 428, 219/429, 430, 436, 521, 528, 530, 535, 549; 435/289.1, 288.4, 286.1, 305.3, 305.4

(56) References Cited

U.S. PATENT DOCUMENTS

| | | | | |
|---|---|---|---|---|
| 4,195,131 A | | 3/1980 | Papas | 435/291 |
| 4,365,665 A | | 12/1982 | Nakamura | 165/80 B |
| 4,865,986 A | | 9/1989 | Coy et al. | 435/290 |
| 4,950,608 A | | 8/1990 | Kishimoto | 435/290 |
| 5,038,852 A | | 8/1991 | Johnson et al. | 165/12 |
| 5,061,630 A | | 10/1991 | Knopf et al. | 435/290 |
| 5,255,976 A | | 10/1993 | Connelly | 374/31 |
| 5,333,675 A | | 8/1994 | Mullis et al. | 165/12 |
| 5,475,610 A | | 12/1995 | Atwood et al. | 364/500 |
| 5,525,300 A | | 6/1996 | Danssaert et al. | 422/99 |
| 5,552,580 A | * | 9/1996 | Pfost et al. | 219/521 |
| 5,602,756 A | | 2/1997 | Atwood et al. | 364/500 |
| 5,616,301 A | | 4/1997 | Moser et al. | 422/104 |
| 5,656,493 A | | 8/1997 | Mullis et al. | 435/286.1 |
| 5,710,381 A | | 1/1998 | Atwood et al. | 73/864.91 |
| 5,779,981 A | | 7/1998 | Danssaert et al. | 422/99 |
| 5,785,926 A | | 7/1998 | Seubert et al. | 422/100 |

(List continued on next page.)

FOREIGN PATENT DOCUMENTS

| | | | |
|---|---|---|---|
| EP | 438883 | 7/1991 | B01D/1/30 |
| EP | 488769 | 6/1992 | C12Q/1/68 |
| EP | 0955097 A1 * | 11/1999 | |
| JP | 05-168459 | 7/1993 | C12M/1/00 |
| JP | 07-308183 | 11/1995 | C12M/1/00 |
| JP | 09/322755 | 12/1997 | C12M/1/00 |
| WO | WO 98/12502 | 12/1989 | B01L/7/00 |
| WO | WO 98/43740 | 10/1998 | B01L/7/00 |
| WO | WO 00/32312 | 6/2000 | B01L/7/00 |

OTHER PUBLICATIONS

"Multi–functional temperature circulator," KR 2001038297A, abstract and single figure, May 15, 2001.*

*Primary Examiner*—Joseph Pelham
(74) *Attorney, Agent, or Firm*—Palmer & Dodge, LLP; Kathleen M. Williams; David J. Dykeman

(57) ABSTRACT

A flexible heating cover assembly for an apparatus for heating samples of biological material with substantial temperature uniformity includes a housing having a plurality of engageable enclosure components; a resistive heater having a plurality of heater element areas; a heater backing plate providing stability to the resistive heater; a force distribution system that distributes a force over the heater backing plate; and a support plate providing stiffness for the force distribution system, wherein the arrangement of the resistive heater, the heater backing plate, the force distribution system and the support plate provide substantial temperature uniformity among a plurality of sample tubes for receiving samples of biological material. The flexible heating cover assembly improves the uniformity, efficiency, quality, reliability and controllability of the thermal response during thermal cycling of the biological material.

82 Claims, 28 Drawing Sheets

U.S. PATENT DOCUMENTS

| | | | | |
|---|---|---|---|---|
| 5,813,233 | A | 9/1998 | Okuda et al. | 62/3.7 |
| 5,819,842 | A | 10/1998 | Potter et al. | 165/206 |
| 5,849,208 | A | 12/1998 | Hayes et al. | 216/94 |
| 5,851,492 | A | * 12/1998 | Blattner | 435/288.4 |
| 5,928,907 | A | 7/1999 | Woudenberg et al. | 435/91.2 |
| 6,004,512 | A | 12/1999 | Titcomb et al. | 422/63 |
| 6,054,263 | A | 4/2000 | Danssaert et al. | 435/4 |
| 6,093,370 | A | 7/2000 | Yasuda et al. | 422/68.1 |
| 6,106,784 | A | 8/2000 | Lund et al. | 422/104 |
| 6,153,426 | A | * 11/2000 | Heimberg | 435/305.4 |
| 6,337,435 | B1 | 1/2002 | Chu et al. | 136/242 |
| 6,638,761 | B2 | * 10/2003 | Shin et al. | 435/288.4 |
| 6,657,169 | B2 | * 12/2003 | Brown | 219/385 |

* cited by examiner

FLEXIBLE HEATING COVER ASSEMBLY FOR THERMAL CYCLING OF SAMPLES OF BIOLOGICAL MATERIAL

RELATED APPLICATIONS

None.

FIELD OF THE INVENTION

The present invention relates to a heating cover assembly for an apparatus for heating samples of biological material, and more particularly to a flexible heating cover assembly that improves the uniformity, efficiency, quality, reliability and controllability of the thermal response during thermal cycling of DNA samples to accomplish a polymerase chain reaction, a quantitative polymerase chain reaction, a reverse transcription-polymerase chain reaction, or other nucleic acid amplification types of experiments.

BACKGROUND OF THE INVENTION

Techniques for thermal cycling of DNA samples are known in the art. By performing a polymerase chain reaction (PCR), DNA can be amplified. It is desirable to cycle a specially constituted liquid biological reaction mixture through a specific duration and range of temperatures in order to successfully amplify the DNA in the liquid reaction mixture. Thermal cycling is the process of melting DNA, annealing short primers to the resulting single strands, and extending those primers to make new copies of double stranded DNA. The liquid reaction mixture is repeatedly put through this process of melting at high temperatures and annealing and extending at lower temperatures.

In a typical thermal cycling apparatus, a biological reaction mixture including DNA will be provided in a large number of sample wells on a thermal block assembly. It is desirable that the samples of DNA have temperatures throughout the thermal cycling process that are as uniform as reasonably possible. Even small variations in the temperature between one sample well and another sample well can cause a failure or undesirable outcome of the experiment. For instance, in quantitative PCR, one objective is to perform PCR amplification as precisely as possible by increasing the amount of DNA that generally doubles on every cycle; otherwise there can be an undesirable degree of disparity between the amount of resultant mixtures in the sample wells. If sufficiently uniform temperatures are not obtained by the sample wells, the desired doubling at each cycle may not occur. Although the theoretical doubling of DNA rarely occurs in practice, it is desired that the amplification occurs as efficiently as possible.

In addition, temperature errors can cause the reactions to improperly occur. For example, if the samples are not controlled to have the proper annealing temperatures, certain forms of DNA may not extend properly. This can result in the primers in the mixture annealing to the wrong DNA or not annealing at all. Moreover, by ensuring that all samples are uniformly heated, the dwell times at any temperature can be shortened, thereby speeding up the total PCR cycle time. By shortening this dwell time at certain temperatures, the lifetime and amplification efficiency of the enzyme are increased. Therefore, undesirable temperature errors and variations between the sample well temperatures should be decreased.

Prior art heating covers used in PCR heating equipment are simple, stiff, and relatively inexpensive. The prior art designs have mainly involved a stiff metal plate, a simple resistive heater, and an insulating cover. Because quantitative data was not generated, the heating covers did not have to control condensation in the biological samples as precisely as the heating covers used in QPCR equipment. Also, because optical data was not collected, the prior art heating cover designs were not complicated with the need to provide a means to excite and collect the optical data through the heating cover. Prior art heating covers used in QPCR heating equipment are mainly derived from their earlier PCR counterparts that provide a means for optical signal transmission, but, prior art heating covers are still mainly stiff designs which do not provide a uniform force distribution about the sample containers.

Prior art heating covers are difficult to use, expensive, complicated and do not provide uniform thermal contact or uniform force distribution about the sample wells. U.S. Pat. No. 5,475,610 discloses an instrument for performing PCR employing a cover which can be raised or lowered over a sample block. U.S. Pat. No. 5,475,610 does not disclose a cover assembly that is flexible to provide a more uniform thermal contact and force distribution on the sample tube caps. U.S. Pat. No. 5,928,907 discloses a system for carrying out real time fluorescence-based measurements of nucleic acid amplification products. U.S. Pat. No. 5,928,907 does not disclose a cover assembly that is flexible to provide a more uniform thermal contact and force distribution on the sample tube caps. The prior art does not disclose a cover assembly that is flexible to provide a more uniform thermal contact and force distribution on the sample tube caps.

In light of the foregoing, there is a need in the art for a flexible heating cover assembly that enhances the thermal response uniformity, efficiency, quality, reliability and controllability of the DNA sample wells in the thermal cycling apparatus.

SUMMARY OF THE INVENTION

The present invention is a flexible heating cover assembly that improves the uniformity, efficiency, quality, reliability and controllability of the thermal response during thermal cycling of DNA samples to accomplish a polymerase chain reaction, a quantitative polymerase chain reaction, a reverse transcription-polymerase chain reaction, or other nucleic acid amplification types of experiments.

The present invention is a flexible heating cover assembly for an apparatus for heating samples of biological material with substantial temperature uniformity including a housing having a plurality of engageable enclosure components; a resistive heater located within the housing, the resistive heater including a plurality of heater element areas; a heater backing plate engaging the resistive heater and providing protection and stability to the resistive heater; a force distribution system that engages the heater backing plate and distributes a force over the heater backing plate; and a support plate providing stiffness for the force distribution system, wherein the arrangement of the resistive heater, the heater backing plate, the force distribution system and the support plate provide substantial temperature uniformity among a plurality of sample tubes for receiving samples of biological material. The flexible heating cover assembly improves the uniformity, efficiency, quality, reliability and controllability of the thermal response during thermal cycling of DNA samples.

In another aspect of the present invention, the resistive heater produces a non-uniform heat distribution along a surface exposed to the plurality of sample tubes. The resistive heater further comprises a plurality of heater element areas including at least one outer heater element area and at least one central heater element area.

In another aspect of the present invention, the heater backing plate is thin to promote flexibility when the heater backing plate is connected to the resistive heater. The heater backing plate is composed of a thermally conductive material.

In another aspect of the present invention, the force distribution system further comprises at least one spring strip and a spring retainer plate. The at least one spring strip has an elongated body and a plurality of spring extensions to distribute the force uniformly on the heater backing plate.

In another aspect of the present invention, the support plate has sufficient stiffness to provide a reaction force for the force distribution system with minimal deflection of the support plate.

In another aspect of the present invention, the resistive heater, the heater backing plate, and the support plate each comprise a plurality of aligned sample well openings, each sample well opening corresponding to a respective sample tube of the plurality of sample tubes.

The present invention is a flexible heating cover assembly with enhanced functions including the flexibility of the cover assembly and the force distribution. In addition, the flexible heating cover assembly of the present invention enables the resistive heater to float in a vertical direction, so that the resistive heater has some freedom of movement vertically which leads to a more uniform thermal contact and force distribution and more accurate and consistent results. The flexible heating cover assembly of the present invention provides thermal insulation for the upper portion of the sample tubes and the sample caps.

BRIEF DESCRIPTION OF THE DRAWINGS

The accompanying drawings, which are incorporated in and constitute a part of this specification, illustrate several embodiments of the invention and together with the description, serve to explain the principles of the invention. The present invention will be further explained with reference to the attached drawings, wherein like structures are referred to by like numerals throughout the several views. The drawings shown are not necessarily to scale, with emphasis instead generally being placed upon illustrating the principles of the present invention.

While the above-identified drawings set forth preferred embodiments of the present invention, other embodiments of the present invention are also contemplated, as noted in the discussion. This disclosure presents illustrative embodiments of the present invention by way of representation and not limitation. Numerous other modifications and embodiments can be devised by those skilled in the art which fall within the scope and spirit of the principles of the present invention.

DETAILED DESCRIPTION

Figure 1:
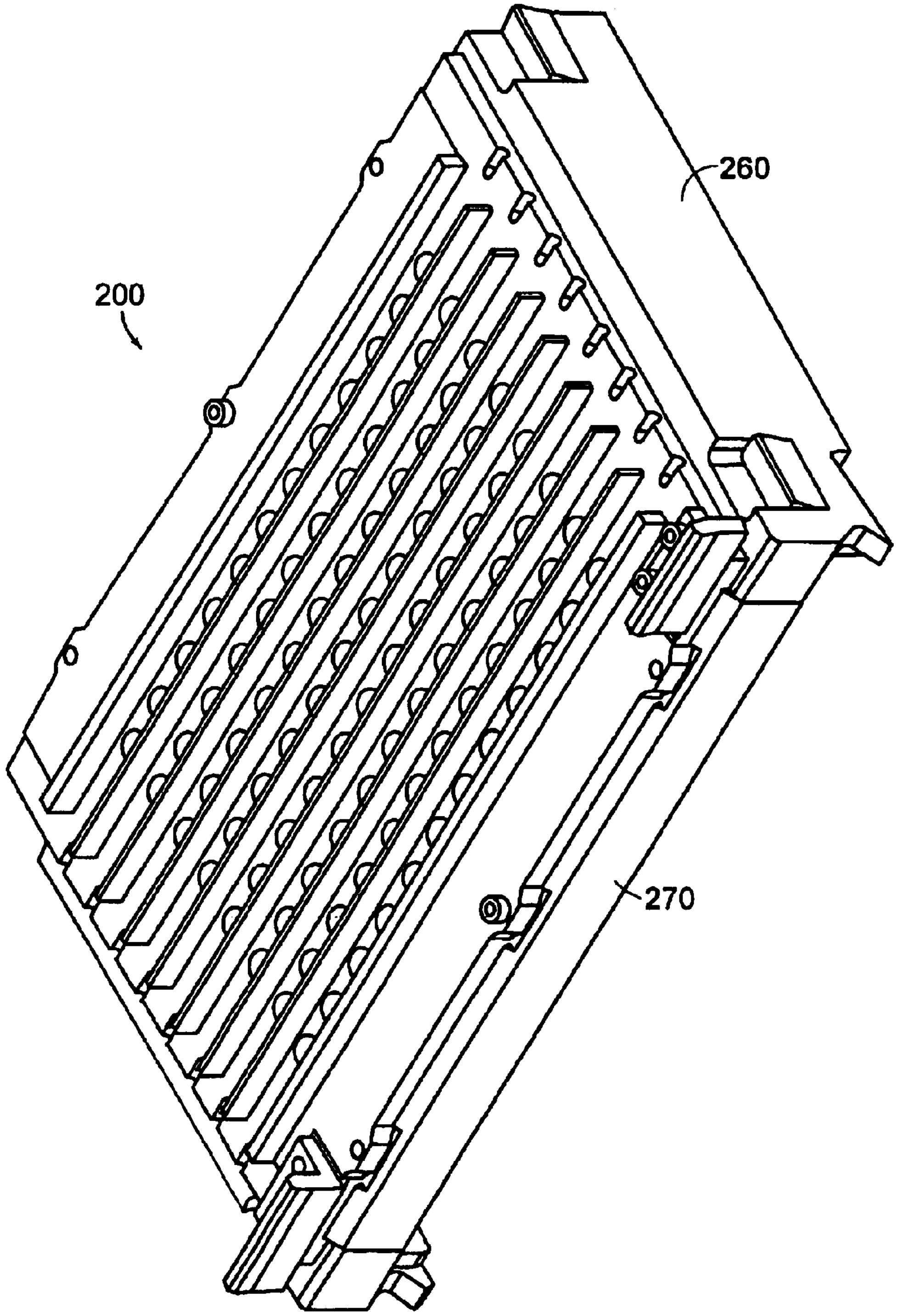
FIG. 1 is a top perspective view of a flexible heating cover assembly of the present invention.
Figure 2:
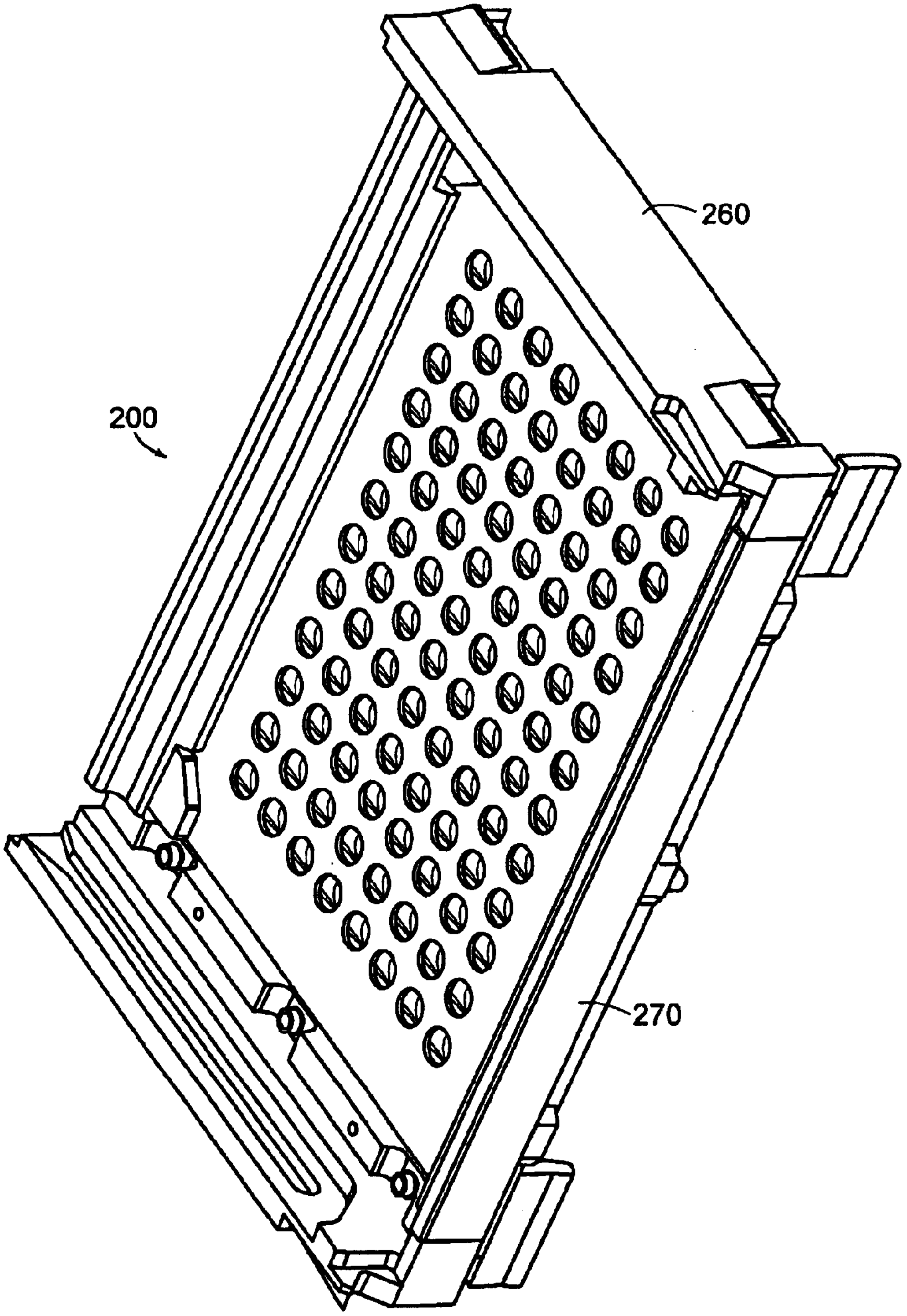
FIG. 2 is a bottom perspective view of a flexible heating cover assembly of the present invention.
Figure 20:
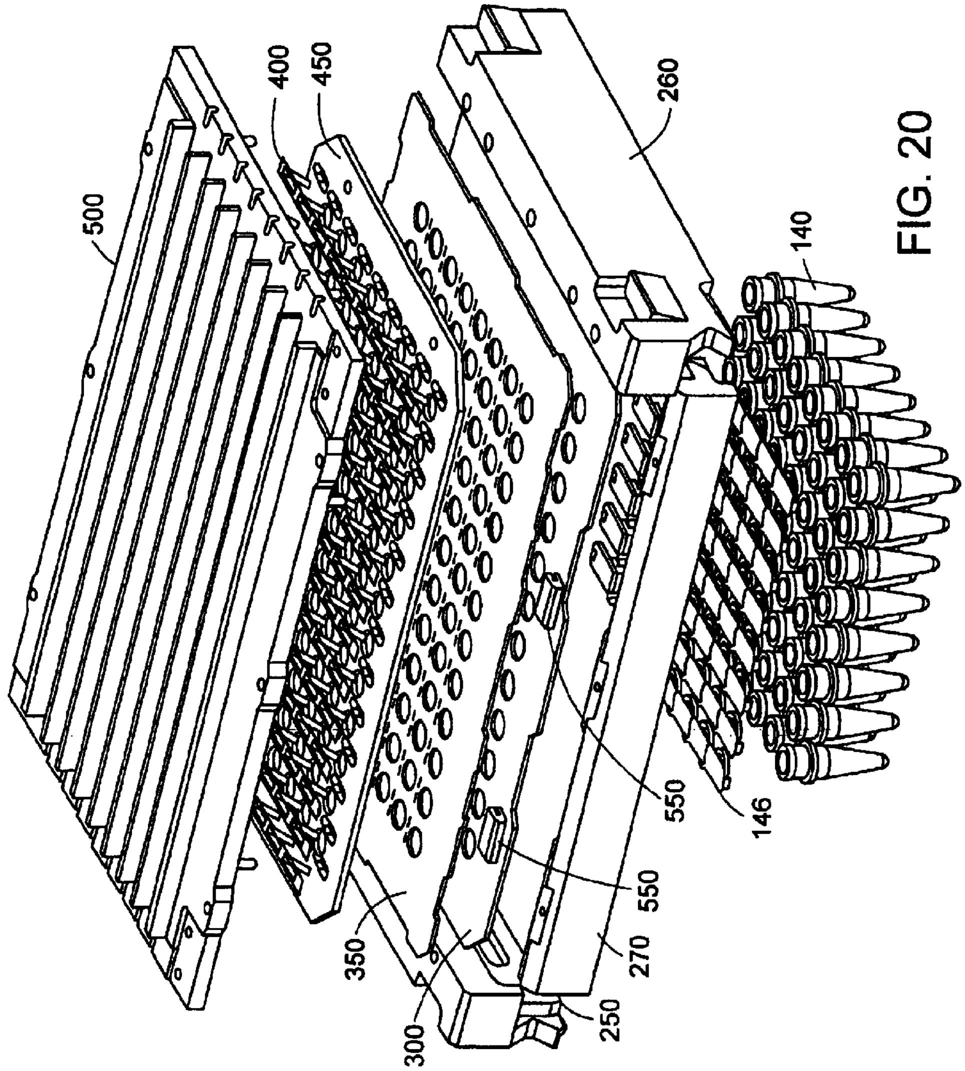
FIG. 20 is a top exploded assembly view of a flexible heating cover assembly of the present invention showing how a stiff support plate, a spring strip, a spring retainer plate, a heater backing plate, a plurality of heater slides, a resistive heater, a cover assembly skirt interact with a plurality of biological sample tubes having sample caps.
Figure 21:
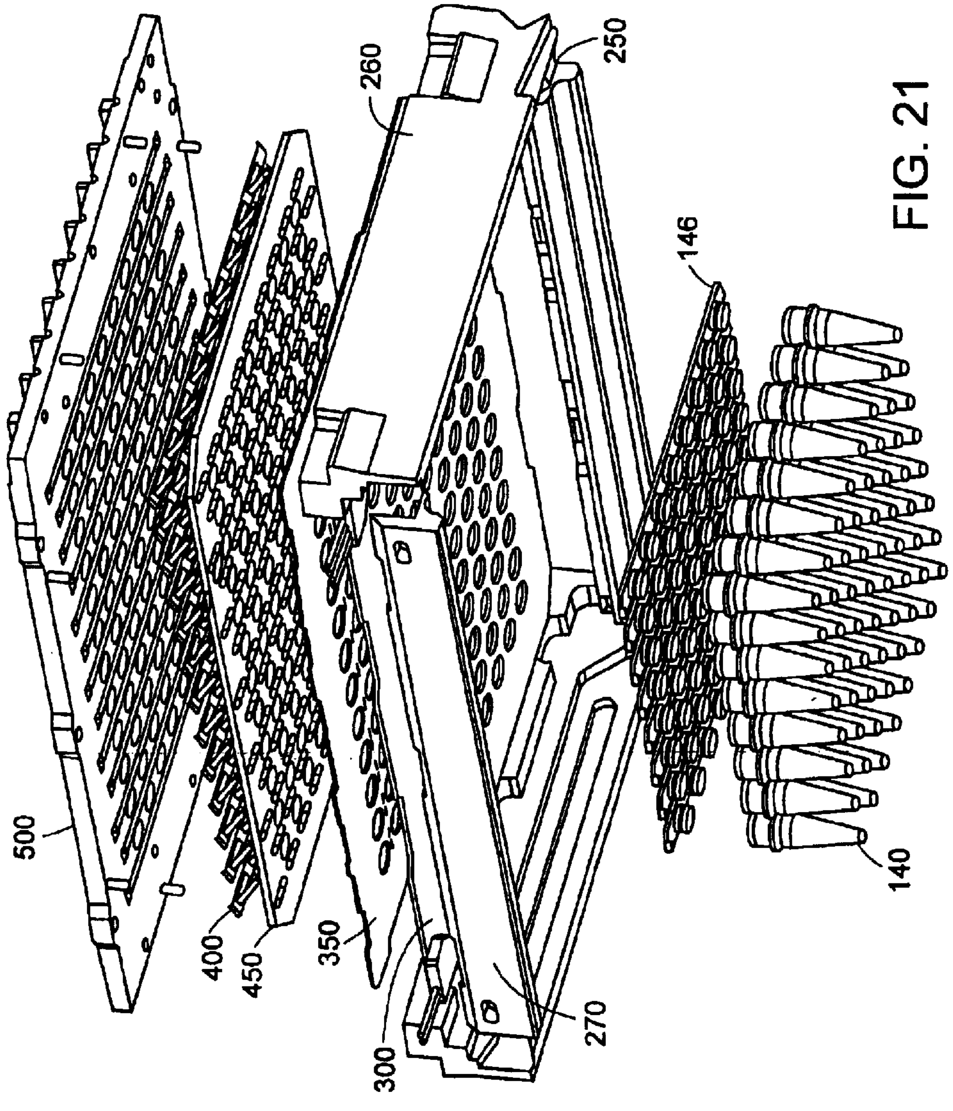
FIG. 21 is a bottom exploded assembly view of a flexible heating cover assembly of the present invention showing how a stiff support plate, a spring strip, a spring retainer plate, a heater backing plate, a plurality of heater slides, a resistive heater, a cover assembly skirt interact with a plurality of biological sample tubes having sample caps.

A flexible heating cover assembly of the present invention is illustrated generally at 200 in FIGS. 1 and 2. As best shown in FIGS. 20 and 21, the flexible heating cover assembly 200 includes a cover assembly skirt 250, a resistive heater 300, a heater backing plate 350, a spring strip 400, a spring retainer plate 450, a stiff support plate 500, and a plurality of heater slides 550. The flexible heating cover assembly 200 engages a plurality of biological sample tubes 140 having sample caps 146.

Figure 3:
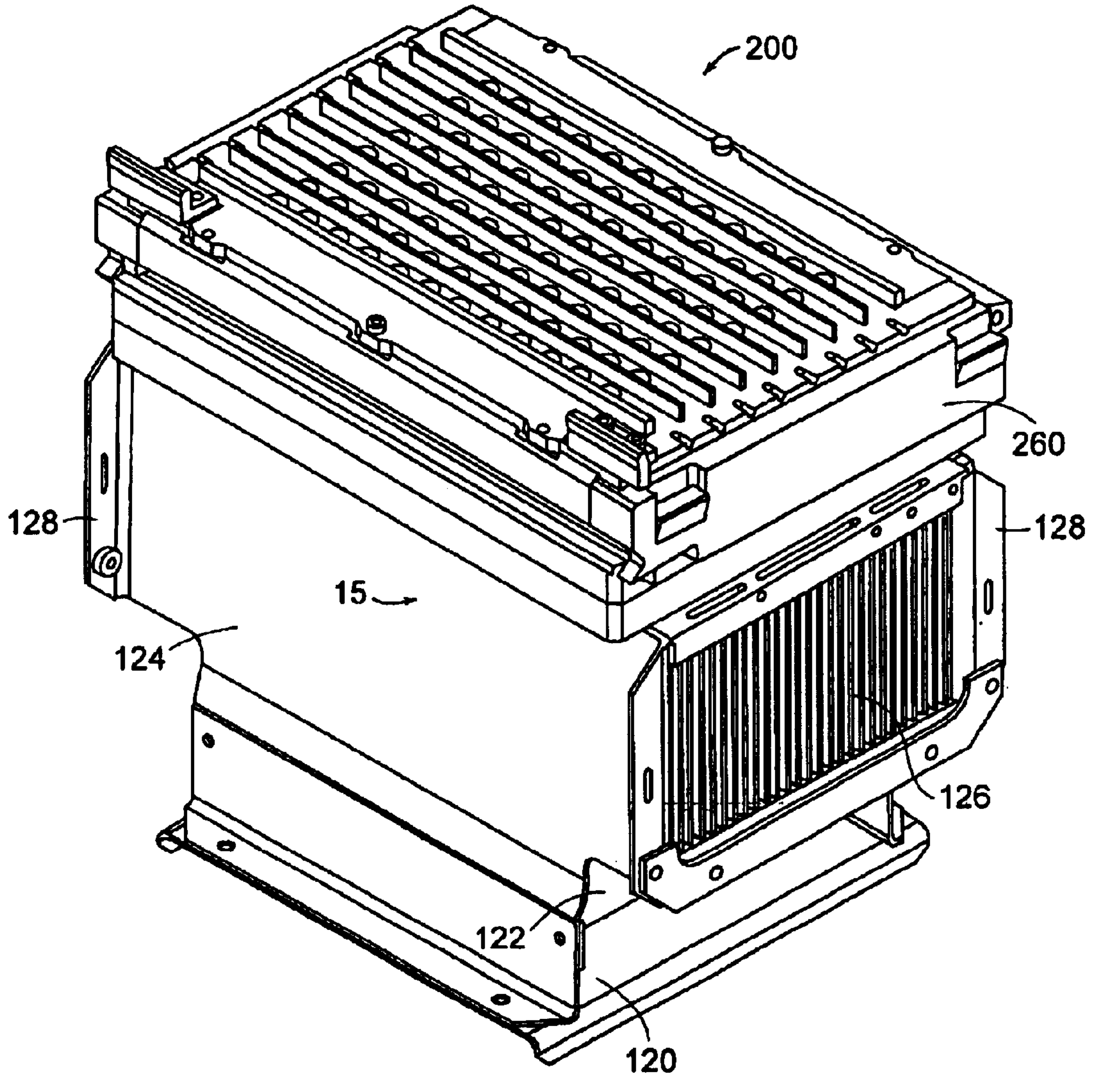
FIG. 3 is a perspective view of a flexible heating cover assembly of the present invention attached to an apparatus for thermally cycling samples of a biological material.

As shown in FIG. 3, the flexible heating cover assembly 200 can be attached to an apparatus for thermally cycling samples of a biological material. The flexible heating cover assembly 200 can be attached to any apparatus for thermal cycling of DNA samples to accomplish a polymerase chain reaction, a quantitative polymerase chain reaction, a reverse transcription-polymerase chain reaction, or other nucleic acid amplification types of experiments. For example, the flexible heating cover assembly 200 can be attached to the apparatus for thermally cycling samples of a biological material disclosed in assignee's co-pending U.S. patent application Ser. No. 09/364,051, the entirety of which is hereby incorporated by reference. When combined with a thermal system base 15 (which contains a thermal block assembly 20 for accepting samples and means to heat and cool the thermal block assembly 20), the flexible heating cover assembly 200 improves the quality of the thermal response of the system for quantitative PCR.

Figure 4:
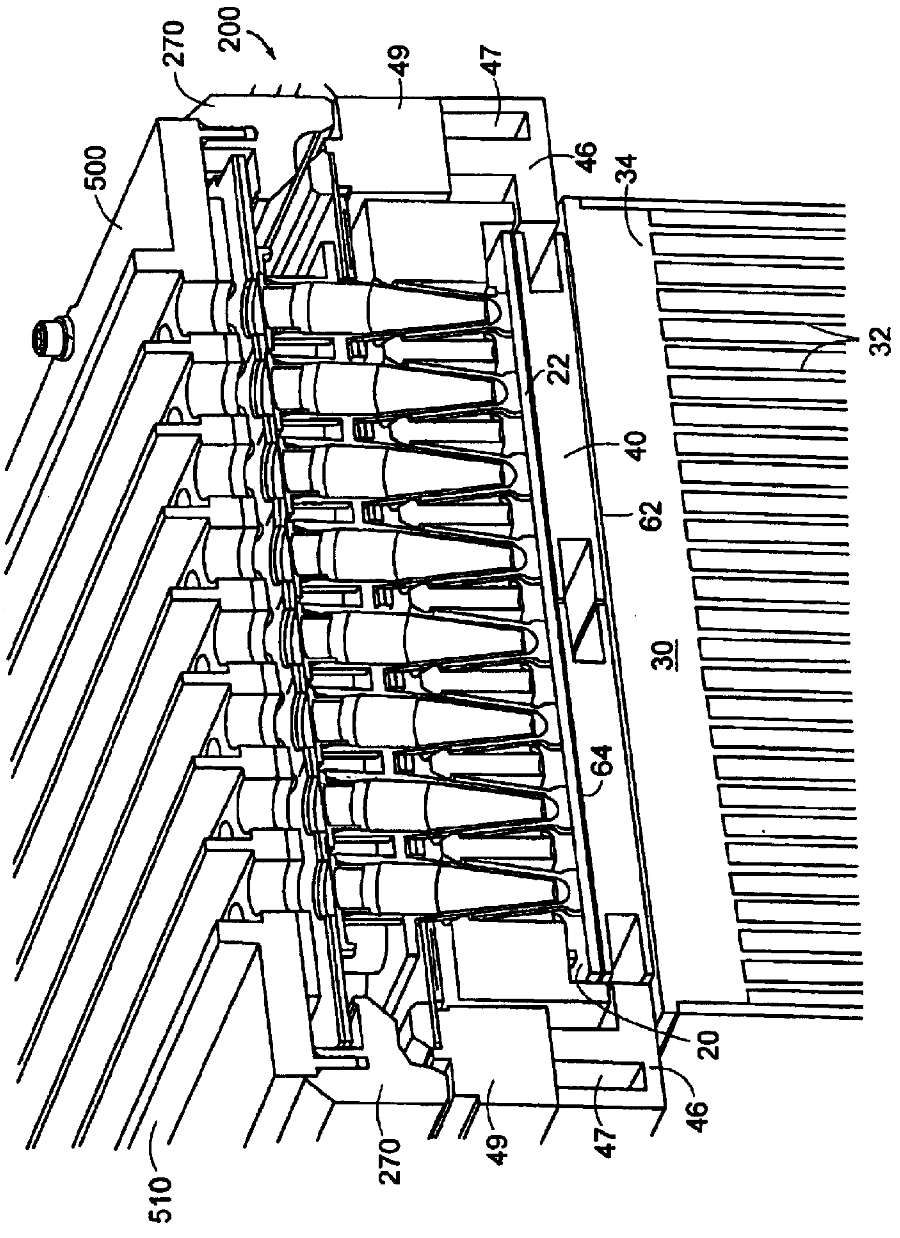
FIG. 4 is a front sectional view of a flexible heating cover assembly of the present invention attached to an apparatus for thermally cycling samples of a biological material.
Figure 5:
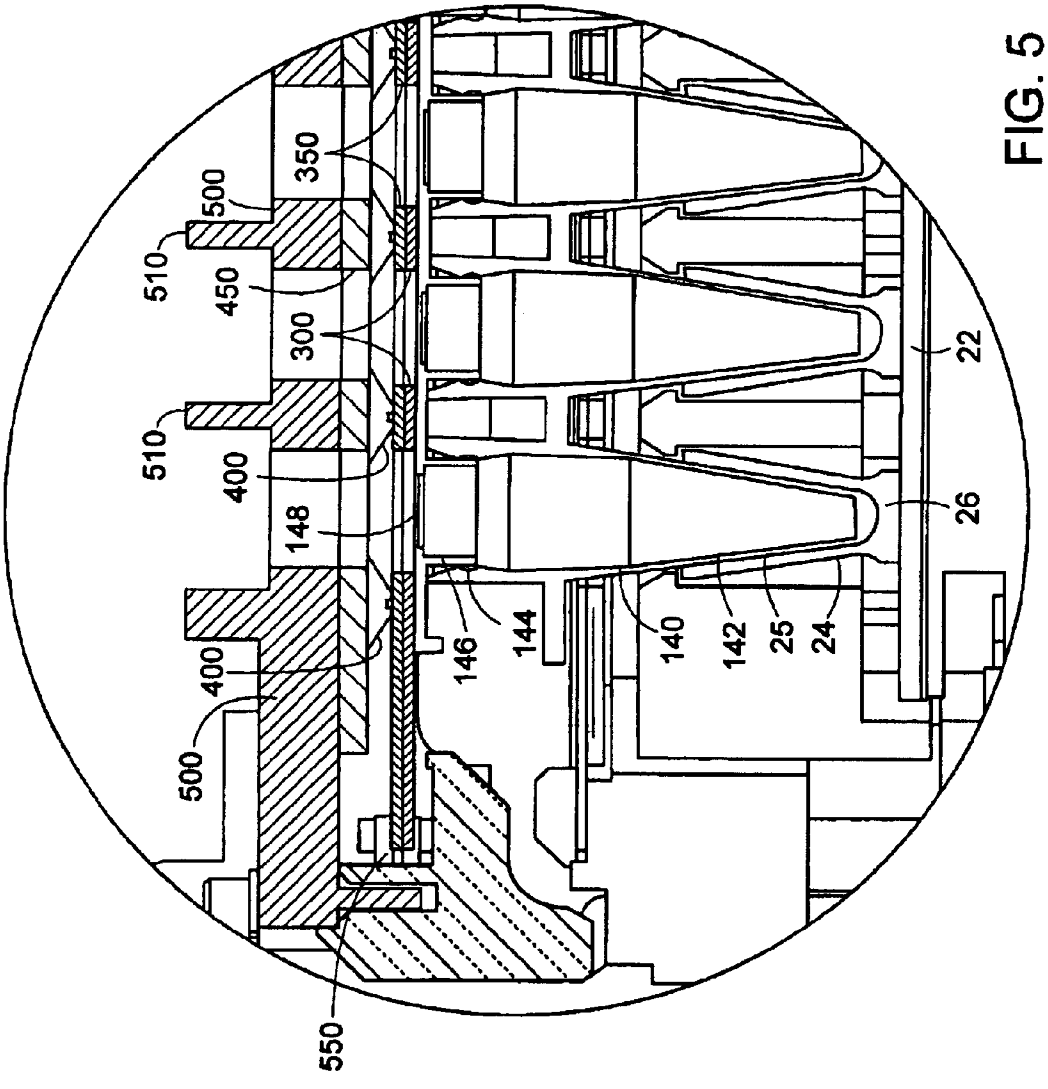
FIG. 5 is a partial enlarged front sectional view of a flexible heating cover assembly of the present invention.
Figure 7:
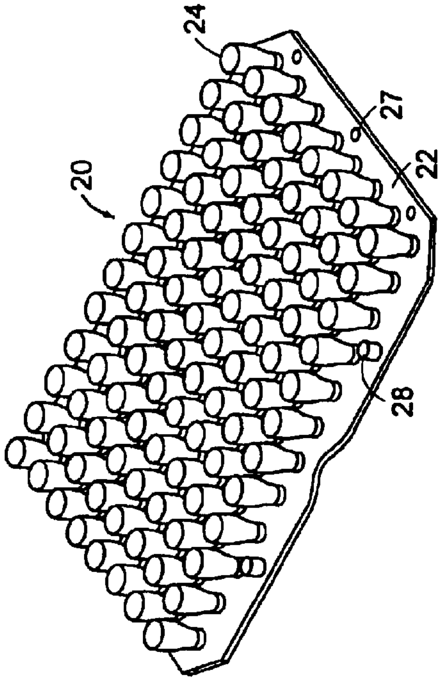
FIG. 7 is a perspective view of a thermal block assembly of a thermal system base.
Figure 6:
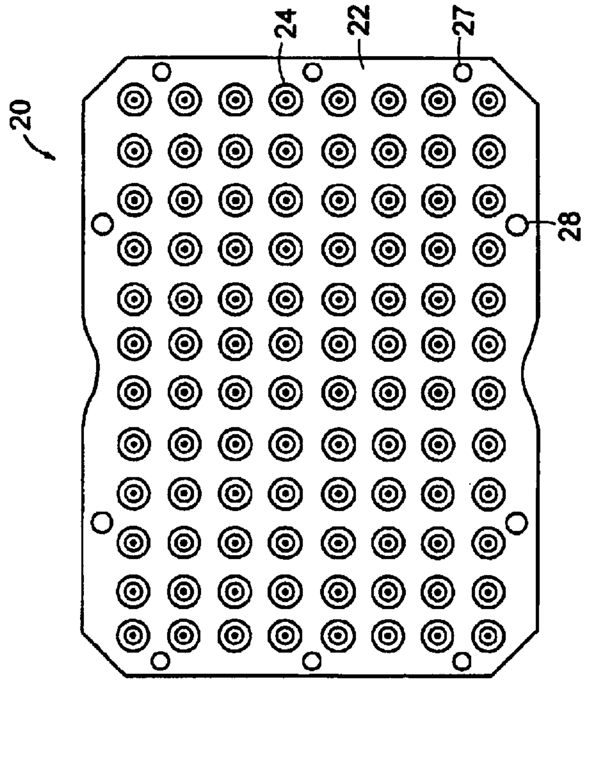
FIG. 6 is a top view of a thermal block assembly of a thermal system base.
Figure 8:
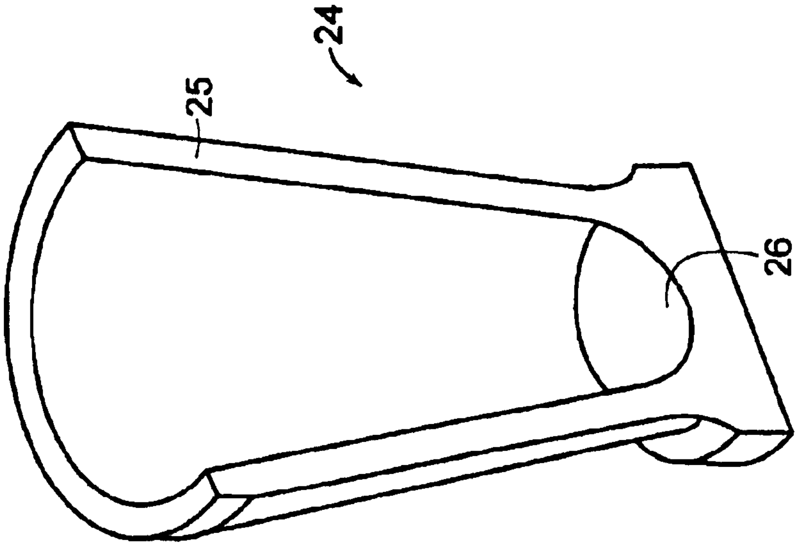
FIG. 8 is a perspective sectional view of a sample well of a thermal system base.

The thermal system base 15 includes a plurality of sample wells for receiving sample tubes of a biological reaction mixture. As shown in FIGS. 3–5, the thermal system base 15 includes a thermal block assembly 20. Thermal block assembly 20 includes a flat thermal block plate 22 and a plurality of sample wells 24 for receiving tubes with samples of DNA, as best shown in FIGS. 4, 6 and 7. Thermal block plate 22 is substantially rectangular and is of sufficient size to accommodate a plurality of sample wells 24 on the top surface, but could be of other shapes (i.e., circular, oval, square). In the embodiment shown in the drawings, the plate 22 accommodates 96 sample wells 24 in a grid having eight columns and twelve rows. The sample wells 24 are in an 8 by 12 grid with center-to-center spacing between adjacent sample wells 24 of about nine millimeters. In other embodiments of the present invention, there may be more or less than 96 sample wells, the sample well arrangement may vary, and the center-to-center measurement between adjacent sample wells 24 may be more or less than nine millimeters. It is to be understood that the number of sample wells can be varied depending on the specific application requirements. For example, the sample wells could be arranged to form a grid which is sixteen by twenty-four, thereby accommodating 384 sample wells. The sample wells 24 are conical in shape, as shown in FIG. 8. The walls 25 of the tube are conical, and extend at an angle to the flat plate 22. The bottom 26 of the interior of the sample well is rounded. The bottom of each sample well 24 is attached to the thermal block plate 22. It should be understood that the sample wells 24 could have any shape (i.e., cylindrical, square or similar shapes), so that the inner surface of the sample wells 24 closely mates with the sample tube 140 inserted inside.

The sample wells 24 are designed so that sample tubes 140 with DNA samples can be placed in the sample wells 24. FIG. 5 shows a partial cut-away cross section with sample tubes 140 placed in the sample wells 24. Each sample well 24 is sized to fit the sample tube 140 exterior so that there will be substantial contact area between the sample tube 140 and the interior portion of a sample well wall 25 to enhance the heat transfer to the DNA sample in the sample tube 140 and reduce differences between the DNA mixture and sample well temperatures. The sample tube 140 includes a conical wall portion 142 which closely mates with the sample well wall 25.

The sample tubes 140 are available in three common forms: (1) single tubes; (2) strips of eight tubes which are attached to one another; and (3) tube trays with 96 attached sample tubes. The present invention is preferably designed to be compatible with any of these three designs. The sample tubes 140 may be composed of a plastic, preferably molded polypropylene, however, other suitable materials are acceptable. A typical sample tube 140 has a fluid volume capacity of approximately 200 $\mu$l, however other sizes and configurations can be envisaged within the spirit and scope of the present invention. The fluid volume typically used in an experiment is substantially less than the 200 $\mu$l sample tube capacity.

Although the preferred embodiment uses sample wells, other sample holding structures such as slides, partitions, beads, channels, reaction chambers, vessels, surfaces, or any other suitable device for holding a sample can be envisaged. Moreover, although the preferred embodiment uses the sample holding structure for biological reaction mixtures, the samples to be placed in the sample holding structure are not limited to biological reaction mixtures. Samples could include any type of product for which it is desired to heat and/or cool, such as cells, tissues, microorganisms or non-biological product.

Alternatively, a thin film of clear or opaque material could be attached (to form a seal) to the tops of the sample containers in place of a series of caps. This type of sample container cover can reduce the labor associated with cap installation for some users. The flexible heating cover assembly of the present invention works with this type of sealed film container cover. Typically, these films are composed of a thin plastic with a layer of epoxy which can be cured using heat, pressure, heat and pressure, or UV light.

As embodied herein and shown for example in FIG. 5, each sample tube 140 also has a corresponding sample tube cap 146 for maintaining the biological reaction mixture in the sample tube. The caps 146 are typically inserted inside a top cylindrical surface 144 of the sample tube 140. The caps 146 are relatively clear so that light can be transmitted through the cap 146. The sample tube caps 146 may be composed of a plastic, preferably molded polypropylene, however, other suitable materials are acceptable. Each cap 146 has an optical window 148 on the top surface of the cap. The optical window 148 in the cap 146 is thin, flat, composed of plastic, and allows radiation such as excitation light to be transmitted to the DNA samples and emitted fluorescent light from the DNA to be transmitted back to an optical detection system during cycling.

A biological probe can be placed in the DNA samples so that fluorescent light is transmitted in and emitted out as the strands replicate during each cycle. A suitable optical detection system can detect the emission of radiation from the sample. The detection system can thus measure the amount of DNA which has been produced as a function of the emitted fluorescent light. Data can be provided from each well and analyzed by a computer.

As best shown in FIGS. 6 and 7, the thermal block plate 22 is provided with mounting holes 27. Attachment screws or other fasteners pass through each of the mounting holes 27. The arrangement of these fasteners will be discussed in greater detail below.

Figure 9:
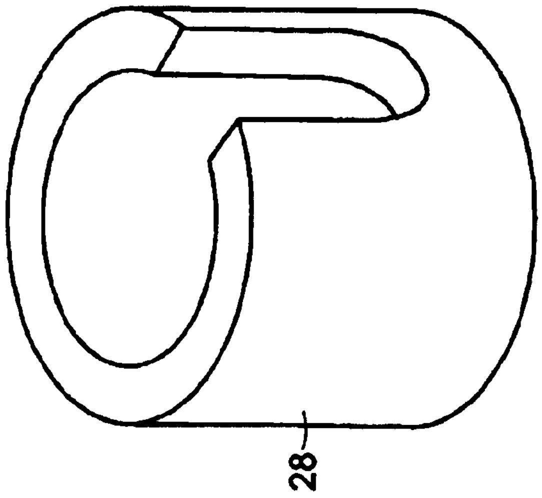
FIG. 9 is a perspective view of a sensor cup of a thermal system base.

As best shown in FIGS. 6, 7, and 9, the thermal block assembly 20 further includes a plurality of sensor cups 28. The sensor cups 28 are positioned adjacent the outer periphery of the thermal block plate 22. In the illustrated embodiment, four sensor cups 28 are positioned outside the grid of sample wells 24. There is at least one sensor cup for each thermoelectric or solid state heating device used to heat the thermal block assembly 20. The details of the solid state heating devices will be discussed below. In the illustrated embodiment, four solid state heating devices are used, and it is therefore appropriate to use at least four thermal sensors in the sensor cups 28. If more solid state heating devices were used, then it would be desirable to have more sensor cups 28. Each of the solid state heating devices may heat at slightly different temperatures, therefore the provision of a thermal sensor in a sensor cup 28 for each solid state heater increases thermal block temperature uniformity.

The sensor cups 28 each include a thermistor or other suitable temperature sensor positioned to measure the temperature of the thermal block plate. Alternate temperature sensors include, but are not limited to, thermocouples or resistance temperature detectors (RTD). Each type of temperature sensor has advantages and disadvantages. The temperature of the thermal block plate 22 at the sensor cup 28 corresponds to the temperature of adjacent sample wells 24. The temperature data from the sensor cup 28 is sent to a controller which will then adjust the amount of heat provided by the heating devices.

The thermal block plate 22, the sample wells 24, and the sensor cups 28 are preferably composed of copper alloy with a finish of electroplated gold over electroless nickel, although other materials having a high thermal conductivity are also suitable. This composition increases the thermal conductivity between the components and prevents corrosion of the copper alloy, resulting in faster heating and cooling transition times. It is important for the thermal block assembly 20 to have a thermal conductivity chosen to increase the temperature uniformity of the sample wells 24. Increasing thermal block temperature uniformity increases the accuracy of the DNA cycling techniques. It is desirable to obtain substantial thermal block temperature uniformity among the sample wells 24. For example, in a thermal block assembly 20 with 96 sample wells with 200μl capacity sample wells being used to thermally cycle samples of DNA, it is typically desirable to obtain temperature uniformity of approximately plus or minus 0.5° C.

The sample wells 24 and sensor cups 28 are fixed to the top surface of the thermal block plate 22. Preferably, the sample wells 24 and sensor cups 28 are silver brazed to the thermal block plate 22 in an inert atmosphere, although other suitable-methods for fixing the sample wells and sensor cups are known. For example, the design of the thermal system base 15 is well suited for a fixing method involving ultrasonic welding. In this ultrasonic welding method, the sample wells 24 are attached to the thermal block plate 22 using pressure and mechanical vibration energy. Many copper alloys and other non-ferrous alloys are well suited for this method. Ultrasonic welding provides the advantages of excellent repeatability and minimal impact to the original material properties because no significant heating is required. Another sample well fixing method involves a copper casting process. Copper casting would require design-changes in the geometry of the sample wells 24. Although the casting process would be less expensive than the silver brazing method, there will be a loss in performance. Therefore, the silver brazing method described above is the preferred method for fixing the sample wells 24 to the thermal block plate 22.

Figure 10:
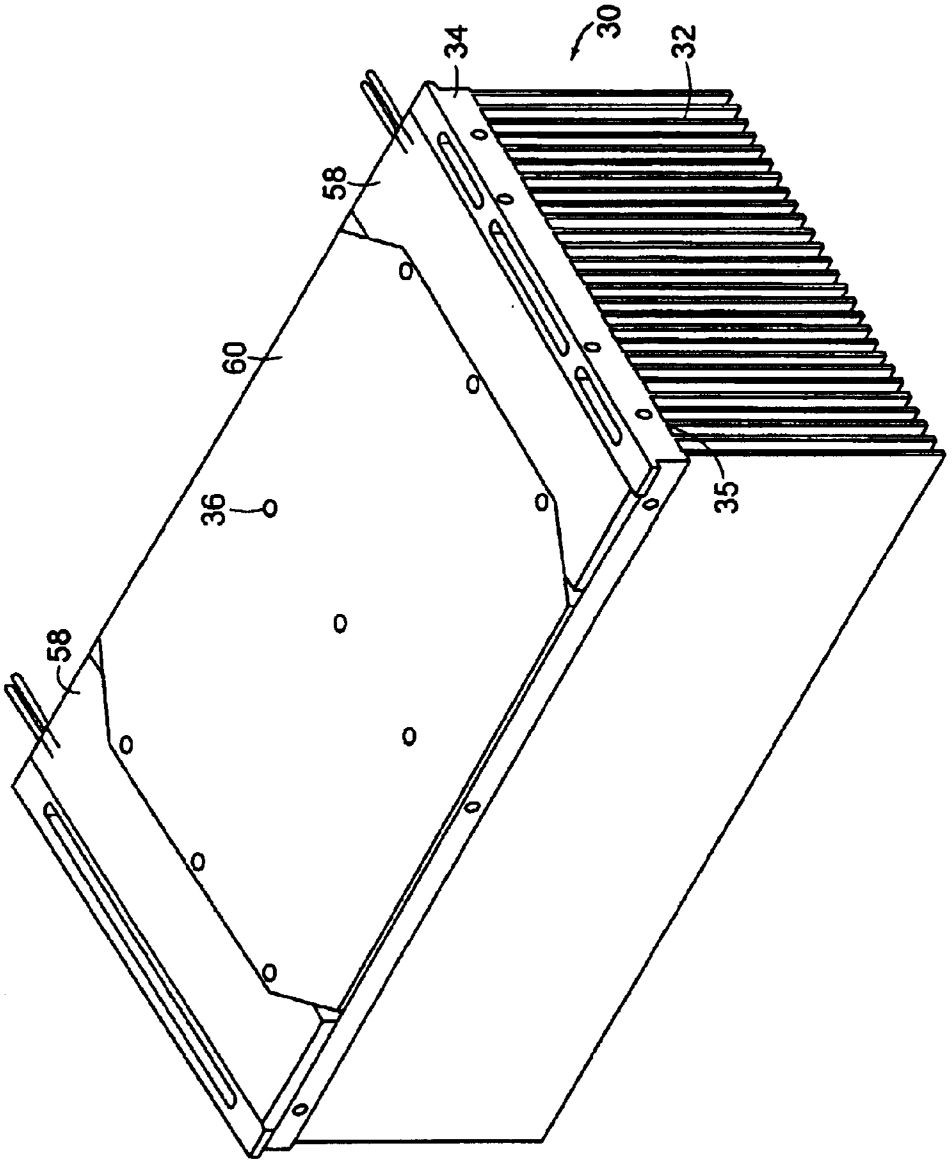
FIG. 10 is a perspective view of a heat sink of a thermal system base.
Figure 11:
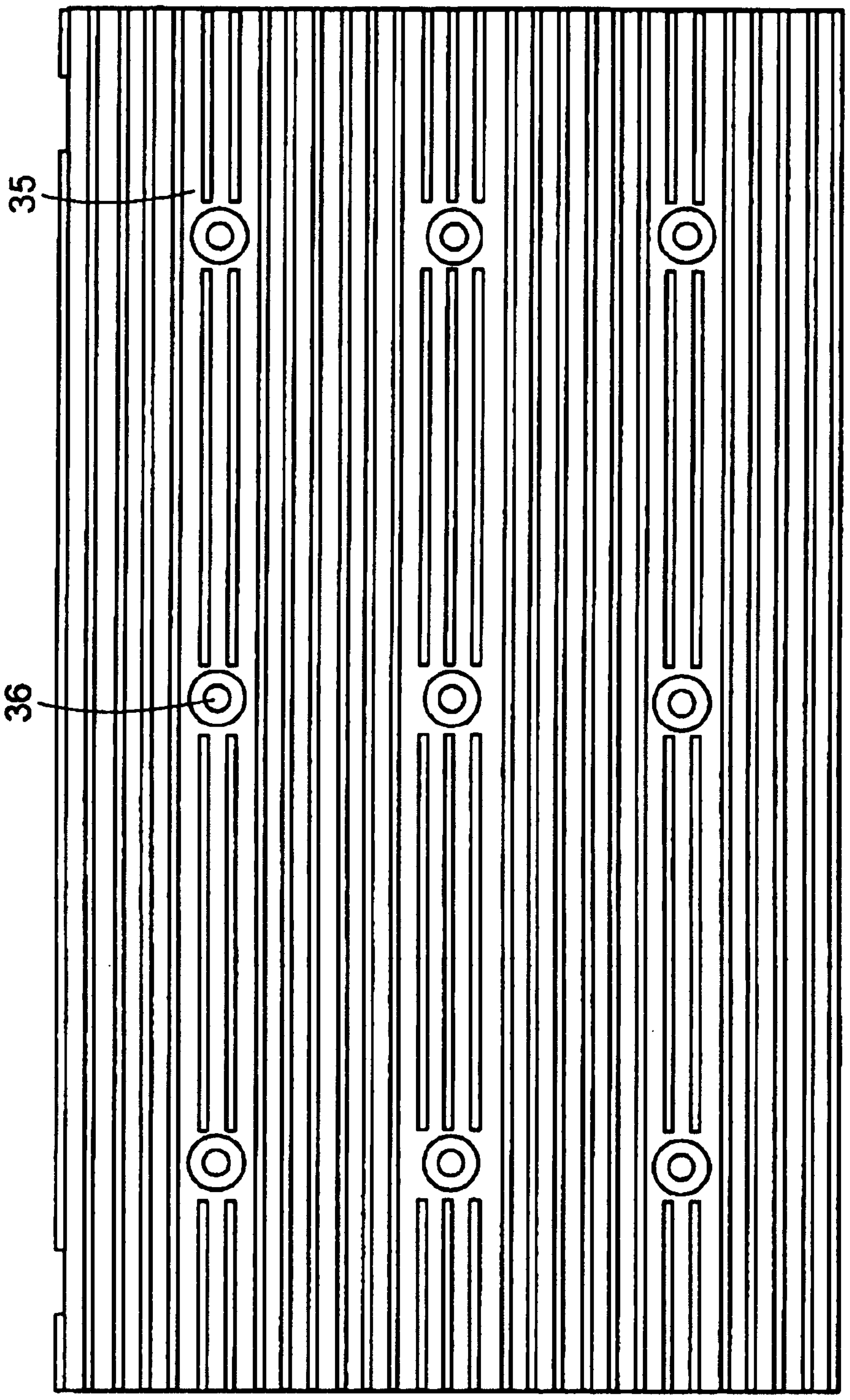
FIG. 11 is a bottom view of a heat sink of a thermal system base.
Figure 13:
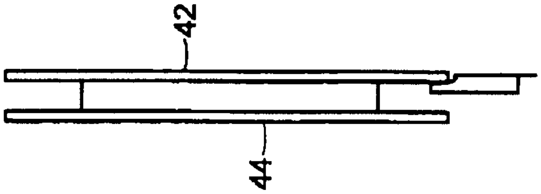
FIG. 13 is a side view of a solid state heater a heat sink of a thermal system base.
Figure 14:
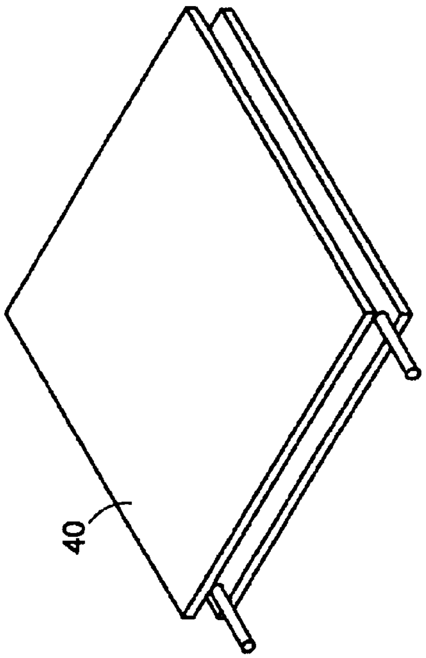
FIG. 14 is a perspective view of a solid state heater of a thermal system base.
Figure 12:
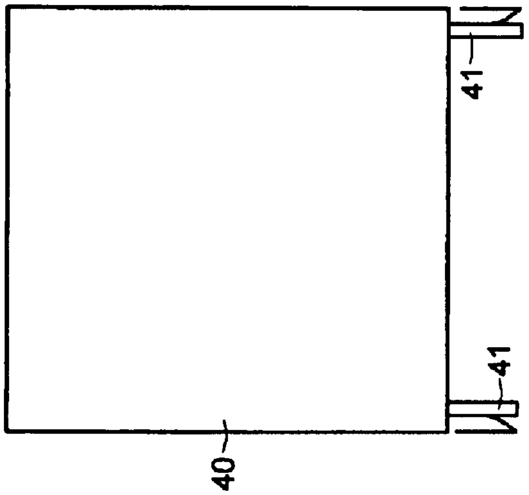
FIG. 12 is a top view of a solid state heater a heat sink of a thermal system base.

As shown in FIGS. 4 and 10–11, a heat sink 30 transfers heat from the thermal block assembly 20 to ambient air located adjacent to the heat sink 30. The heat sink 30 includes a plurality of parallel, rectangular fins 32 extending downward from a base 34. It should be understood that the heat sink 30 may be of any well-known type. The heat base 34 and rectangular fins 32 are preferably made from aluminum, although other suitable materials may be used within the spirit and scope of the invention. The heat sink 30 allows the thermal block assembly 20 to be quickly and efficiently cooled during thermal cycling. Heat is transferred from the thermal block assembly 20 to the heat sink 30 due to the lower temperature of the heat sink 30. The heat which flows to the heat sink 30 is dissipated from the heat sink rectangular fins 32 to the ambient air which flows between the fins 32.

The heat sink base 34 includes attachment holes 36 through which fasteners such as attachment screws pass. The attachment holes 36 extend from the top surface 60 to the bottom surface or underside 35 of the heat sink base 34. The details of the attachment means will be described later.

As shown in FIGS. 4, 12–15, and 18–19, at least one solid state heater 40 supplies heat to the thermal block assembly 20. The solid state heaters 40 are preferably thermoelectric heaters, such as Peltier heaters, but could also be any other type of heater including, but not limited to, a resistive heater. The Peltier heaters 40 are preferred because they can be controlled to exhibit a temperature gradient. Another advantage of the Peltier heaters 40 is that Peltier heaters 40 are capable of providing cooling. The Peltier heaters 40 can be controlled to cool the thermal block assembly below the ambient temperature. This cooling is not possible with other types of heaters such as a resistive element heater. This cooling allows the Peltier heaters 40 to pump heat from the thermal block assembly to the heat sink 30. The Peltier heaters 40 achieve cooling by changing the electrical current polarity into the Peltier heaters 40. The convective air current across the heat sink 30 transfers this heat which has been pumped to the heat sink 30 to the ambient air.

Each Peltier heater 40 includes two lead wires 41 for supplying an electrical current through the heater. Each Peltier heater 40 also includes a first side 42 located closer to the thermal block plate 22, and a second side 44 located closer to the heat sink base 34. During heating of the Peltier heater 40, the first side 42 will be hot and the second side 44 will be cool. During cooling by the Peltier heater 40, the first side 42 will be cool and the second side 44 will be hot. As previously discussed, the hot and cold sides are changed with the reversal of the current flow. A plurality of these heaters are located between the heat sink 30 and thermal block assembly 20. The number of Peltier heaters 40 can vary depending on the specific heating and cooling requirements for the particular application. In the illustrated embodiment, four Peltier heaters 40 are provided. The number and shape of the Peltier heaters 40 can be modified. The system could be altered such that a rectangular Peltier heater 40 could be used, alone or in combination with other rectangular or square Peltier heaters 40. Other shapes of Peltier heaters 40 could also be envisaged. Other types of Peltier heaters 40, such as two-stage Peltier heaters 40, could also be envisaged. For example, a two-stage Peltier heater 40 has two levels or stages of heat pumping elements which are separated by a plate. These two-stage Peltier heaters 40 are typically used in order to create very large temperature differences between the cold and hot sides. The Peltier heaters 40 with more than 2 pumping stages are also possible.

Each of the Peltier heaters 40 is controlled independently of the other Peltier heaters 40. Independent heater control is desirable because each Peltier heater 40 may have slightly different temperature characteristics, that is, if identical currents were placed in each of the Peltier heaters 40, each of the Peltier heaters 40 could have a slightly different temperature response. Therefore, by providing temperature control using multiple sensors and sensor cups for the heaters, each Peltier heater 40 can be separately controlled to enhance uniform temperature distribution to the thermal block assembly 20. Alternately, the independent temperature control can be used to set up a plurality of temperature zones with different temperatures.

As shown in FIGS. 4 and 15–17, a spacer, such as a bracket for positioning the at least one solid state heater. A spacer bracket 46 is provided above and adjacent to the heat sink base 34. The spacer bracket 46 is preferably composed of polyetherimide, although other suitable materials are also acceptable. A spacer bracket cover 49 is included above and adjacent to the spacer bracket 46. The spacer bracket 46 includes attachment holes 48 through which fasteners such as the attachment screws pass.

Figure 15:
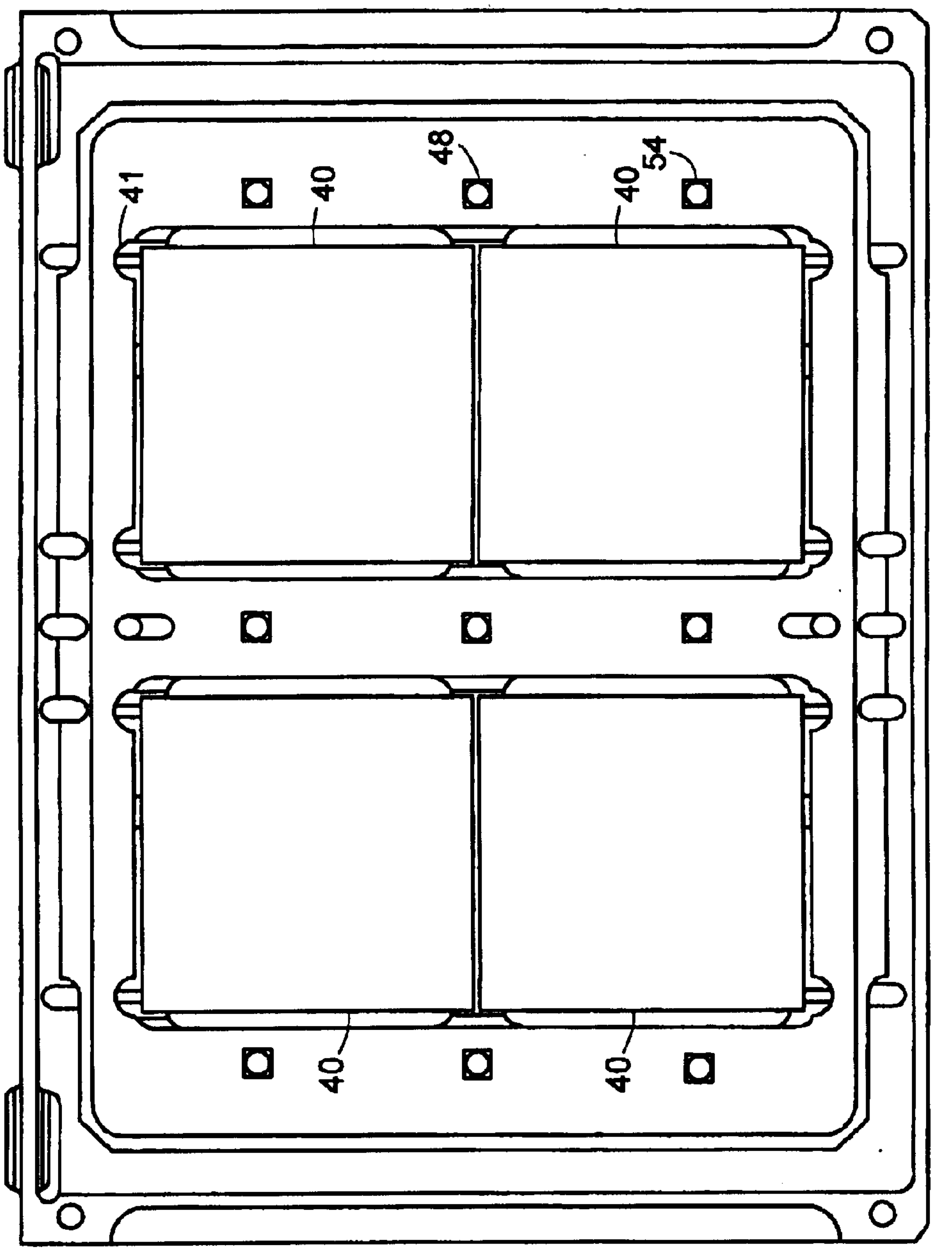
FIG. 15 is a top view of a spacer bracket with a solid state heater of a thermal system base.
Figure 16:
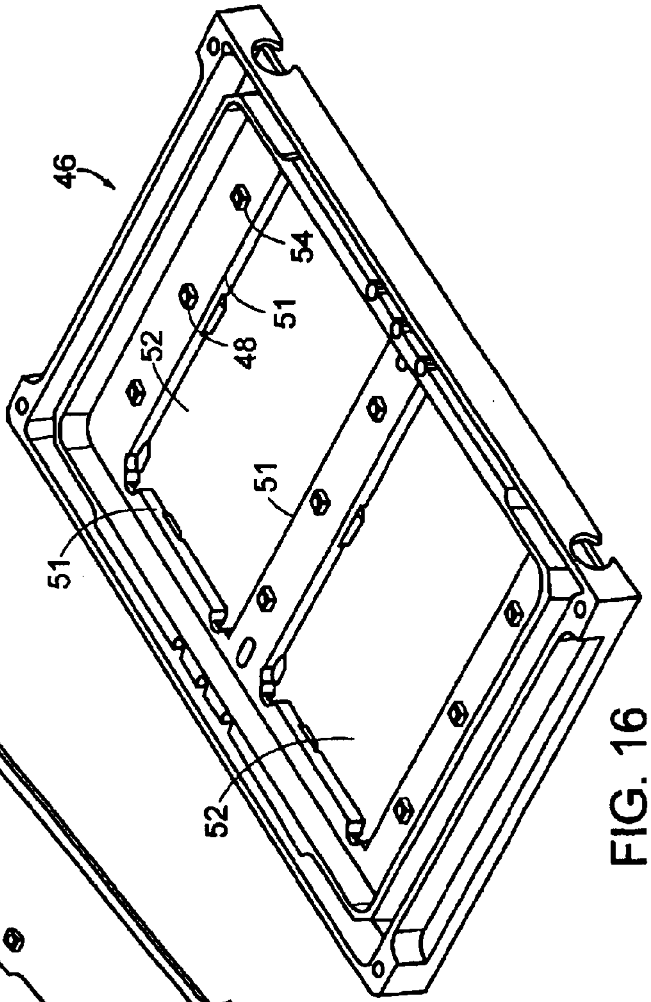
FIG. 16 is a top perspective view of a spacer bracket of a thermal system base.
Figure 17:
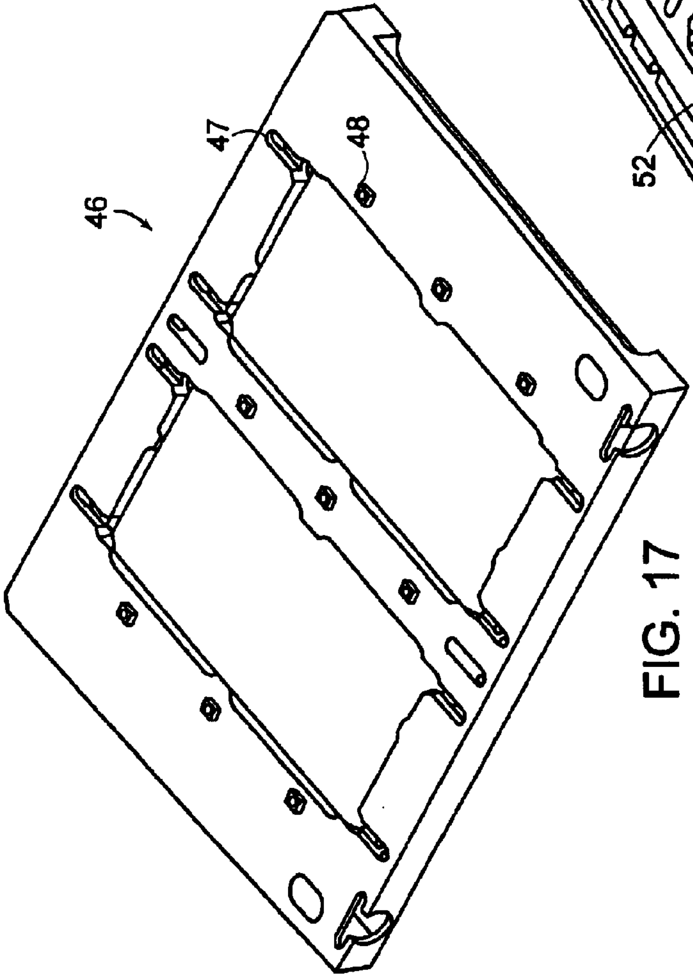
FIG. 17 is a bottom perspective view of a spacer bracket of a thermal system base.

The spacer bracket 46 includes openings 52 in which the Peltier heaters 40 are positioned. As shown in FIG. 15, for example, two Peltier heaters 40 can be positioned in each of the two openings 52. The lead wires 41 of the Peltier heaters 40 are positioned so that they will be received in slots 47 of the spacer bracket. The placement of the lead wires 41 in the slots 47 will prevent significant movement by the Peltier heaters 40 in the bracket, while still allowing slight movement. The slots 47 are dimensioned to be slightly larger than the lead wires 41 to allow such slight movement.

The spacer bracket has bosses 54 around the attachment holes 48 which have a thickness such that the thermal block assembly 20 will be placed in compression. By placing the thermal block assembly 20 in compression, heat transfer can occur more efficiently. For example, by imparting a compressive force, the Peltier heaters 40, the heat sink 30, the thermal block plate 22, and the thermal interface materials will be placed firmly in contact with one another. It should be understood that the spacer bracket 46 can be designed to accommodate a variety of different Peltier heater 40 configurations. The spacer bracket 46 and the Peltier heaters 40 are designed so that a minimum amount of heat is transferred to the spacer bracket 46. As shown in FIG. 15, a small gap is provided between the outside edge of the Peltier heaters 40 and the inner surfaces 51 of the inner walls of the openings 52. The gap reduces the amount of contact between the Peltier heaters 40 and the spacer bracket 46, thereby reducing the amount of heat loss to the spacer bracket 46.

Figure 18:
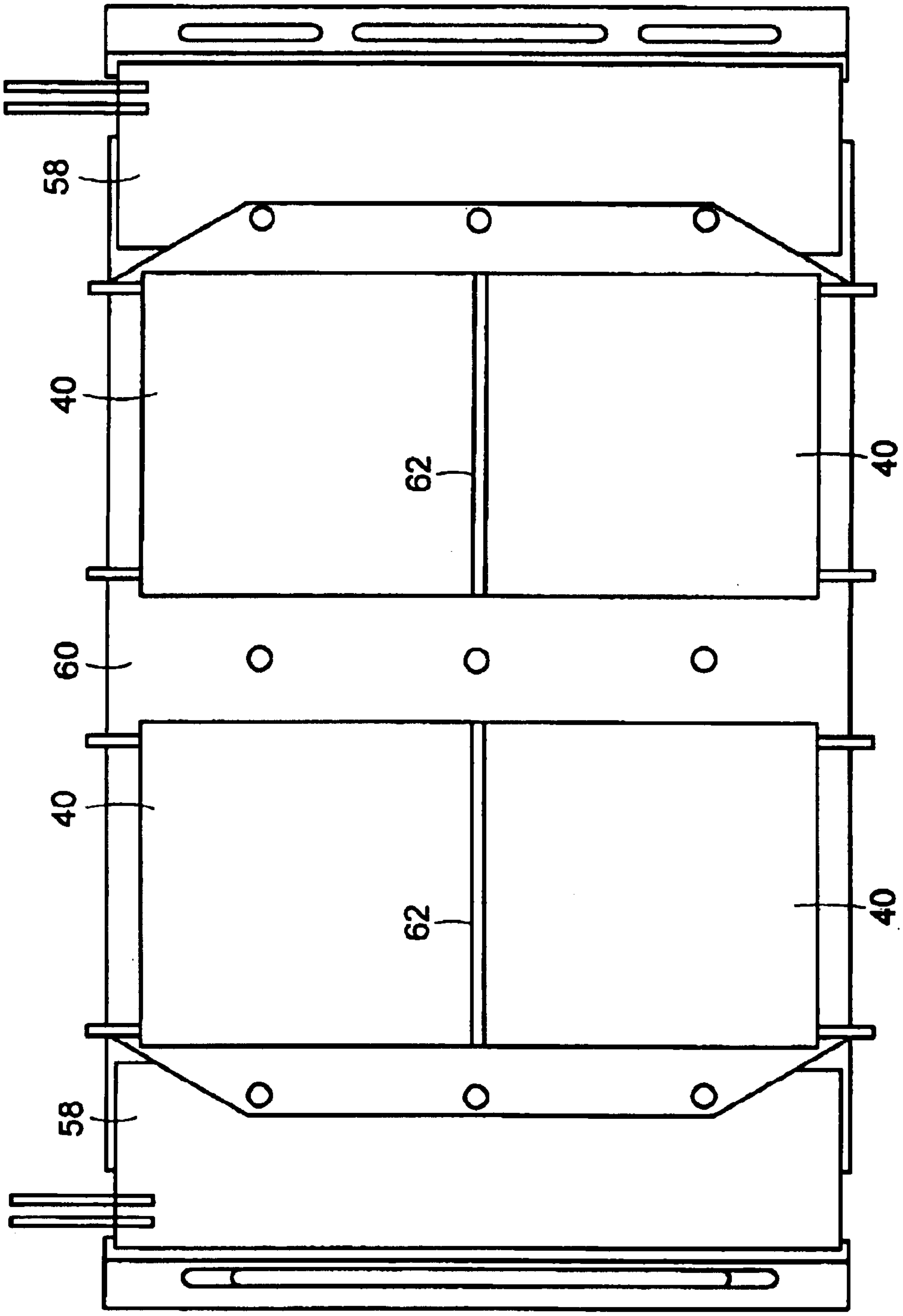
FIG. 18 is a top view of a heat sink, a bottom resistive heater, and a plurality of solid state heaters of a thermal system base.

As shown in FIGS. 4, 10 and 18, a heater is located below the solid state heaters 40 for heating a bottom portion of the solid state heaters 40. A plurality of resistive element heaters 58 are provided on the top surface 60 of the heat sink base 34. It should be understood that any other type of suitable heater may also be used. In the illustrated embodiment, resistive element heaters 58 are placed at the front and back edges of the top surface 60 of the heat sink 30. For the sake of the specification, the front is the portion located adjacent the air exit plate 126 on the right side of in FIG. 3, and the back is the portion located adjacent the opposite air exit plate which cannot be seen in FIG. 3. The positioning of the front and the back resistive element heaters helps to provide thermal block temperature uniformity in a manner described in further detail below.

The Peltier heaters 40 are the primary source used for heating the thermal block plate 22. However, the Peltier heaters 40 are primarily located towards the central portion, in that the Peltier heaters 40 are located in the openings 52 of the spacer bracket 46 as best shown in FIGS. 15–18. In the absence of the bottom resistive heater, the Peltier heaters 40 would be directed primarily to the central portion of the thermal block plate 22, with the risk of decreasing temperatures at the edges of the thermal block plate 22, such as the front and back portions An arrangement for heating the thermal block assembly 20 at the front and back edges to provide thermal block temperature uniformity is also used. Resistive heaters 58 are provided for improving thermal block plate temperature uniformity. The resistive heaters do this by heating the edges of the heat sink on which they are attached. This results in a desired temperature gradient in the heat sink 30. The resistive heaters 58 do not directly heat the front and back portions of the thermal block plate 22 through convection or direct contact. The resistive heaters 58 also do not contact the Peltier heaters 40. The resistive heaters 58 create the temperature gradient in the heat sink 30 by increasing the temperature of the heat sink 30 at the front and back of the heat sink base 34. As a result of the temperature gradient on the heat sink 30, the Peltier heaters 40 transfer a greater amount of heat at the front and back edges of the Peltier heater 40 which are adjacent to the heat sink 30 at the locations closest to the resistive heaters 58. The hot side of the Peltier heaters 40 will have a hotter temperature at the portion of the Peltier heater 40 closest to the resistive heater. Therefore, the front and back portions of the thermal block plate 22 will receive a greater amount of heat transfer than the central portion of the thermal block plate 22. This will ensure that the front and back portions of the thermal block plate 22 which are not adjacent to the Peltier heaters 40 will receive heat transfer by conduction through the thermal block plate 22 and thermal interface elements. It should be understood that the number and position of the resistive element heaters is exemplary only and will vary depending on the design requirements.

As shown in FIGS. 4 and 18, at least one bottom thermal interface element is provided between the bottom of the Peltier heaters 40 and the top surface of the heat sink 30. The bottom thermal interface elements 62 are flat plates positioned between the bottom of the Peltier heaters 40 and the top surface 60 of the heat sink 30. A bottom thermal interface element 62 is provided for each of the openings 52 in the spacer element. Therefore, the two Peltier heaters 40 in the front opening are provided with a plate of thermal interface material, and the two Peltier heaters 40 in the back opening are provided with a second plate of thermal interface material.

Each bottom thermal interface element 62 is slightly smaller than its respective opening 52 in the spacer element. Each bottom thermal interface element roughly corresponds to the size of the surface area of the two Peltier heaters 40 which it covers. For example, as shown in FIG. 18, the bottom thermal interface elements are located immediately underneath the Peltier heaters 40. Only a small portion of the bottom thermal interface element can be shown because the Peltier heaters 40 cover the entire surface area of the bottom thermal interface elements except for the portion located in between the two Peltier heaters 40 sharing the same opening, as shown in FIG. 18.

The bottom thermal interface elements 62 have a high rate of thermal conductivity in order to provide effective heat transfer between heat sink 30 and the Peltier heaters 40. In addition, the material is relatively soft so that the bottom thermal interface elements 62 can be compressed. This allows the Peltier heaters 40 to have a more evenly distributed surface area with the top of the heat sink 30. An example of the type of material to be used in the thermal interface elements is a boron nitride filled silicone rubber. Any other type of suitable material is also acceptable.

Figure 19:
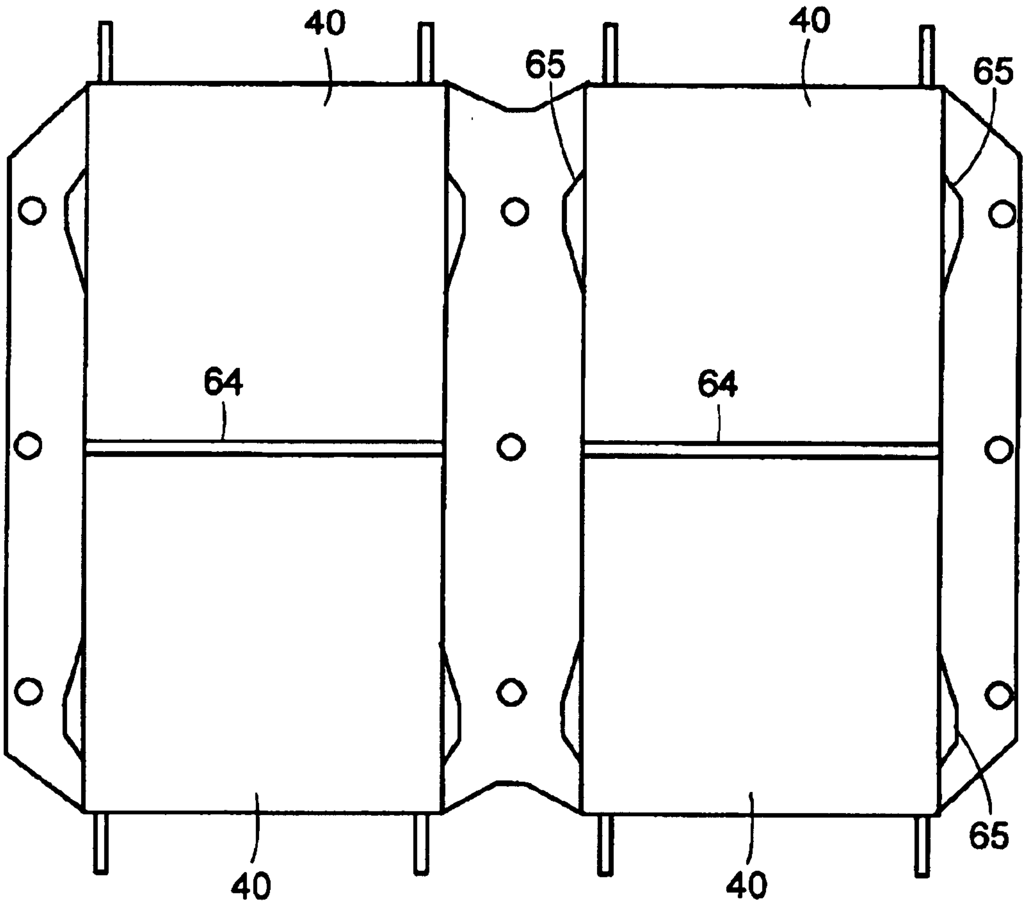
FIG. 19 is a bottom view of a thermal block plate and a plurality of solid state heaters of a thermal system base.

As shown in FIGS. 4 and 19, at least one top thermal interface element 64 is provided between the top of the Peltier heaters 40 and the bottom of the thermal block plate 22. A pair of top thermal interface elements 64 are located between the top of the Peltier heaters 40 and the bottom of the thermal block plate 22. During heating by the Peltier heaters 40, the top thermal interface elements conduct the heat from the first side 42 of the Peltier heaters 40 to the bottom of the thermal block plate 22. The top thermal interface elements 64 are similar in shape and size to the bottom thermal interface elements 62, except for the additional provision of thermal interface wings 65 on the thermal interface elements. The wings are located on the front and back side of each Peltier heater 40. The wings 65 provide heat transfer to the areas of the thermal block plate 22 outside of the Peltier heaters 40. The wings 65 effectively conduct the additional heat that is generated in the heat sink 30 and Peltier heaters 40 at the front and back edges due to the bottom resistive heaters. The wings 65 distribute this heat to the front and back edges of the thermal block plate 22. This increases thermal block temperature uniformity. The top thermal interface elements 64 are composed of the same material with the relatively high rate of thermal conductivity as the bottom thermal interface elements 62.

It should be understood that any number of interface elements, including only one, could be used. The provision of the top and bottom thermal interface elements also allows the Peltier heaters 40 to "float" between the thermal block plate 22 and the heat sink base 34. The compressible thermal interface material provides for effective heat transfer among the surfaces while also uniformly loading the Peltier heaters 40 in compression. The use of the compressible thermal interface material increases cycle life and reliability of the Peltier heaters 40. The thermal interface material improves the reliability of the system by affecting the compressive load imparted onto each Peltier heater 40. Any structural compressive loading forces are dampened and uniformly distributed into the Peltier heaters 40 due to the thickness and elastomeric characteristics of the thermal interface material. Due to the more uniform loads imparted on the Peltier heaters 40, the reliability of the solder joints within each Peltier heater 40 will be improved. It is important not to overly compress the Peltier heater 40 with physical or thermal shock which can result in premature failure.

The thermal system base 15 further includes a radial fan (not shown) to provide air to the heat sink 30. The radial fan is provided adjacent the bottom fan duct 120. The bottom fan duct 120 has an air inlet opening 122 through which ambient air enters. The circulating air flows upward along the interior of the central fan duct 124. The circulating air then enters the spaces between the heat sink rectangular fins 32 and flows along the bottom surface 35 of the heat sink 30. The heat sink 30 transfers heat to the circulating air which then passes out through fan air exit plates 126. The fan air exit plates 126 are bolted onto flanges 128 of the central fan duct 124.

The thermal system base 15 is designed to increase the cycle life and reliability of the Peltier heaters 40. An additional way in which the reliability of the Peltier heaters 40 is improved is by matching the thermal coefficient of expansion of the materials used for the structural components surrounding the Peltier heaters 40. Specifically, the thermal block plate 22, the spacer bracket 46, and the heat sink base 34 have all been designed to have very similar thermal coefficients of expansion. During thermal cycling of a DNA sample, the Peltier heaters 40 are structurally loaded with forces resulting from the expansion and contraction of these components. By providing similar thermal coefficients of expansion to these materials, the expansion and contraction forces on the Peltier heaters 40 are minimized, thereby improving the cycle life of the solder joints within the Peltier heaters 40.

It will be understood that a suitable computer device, such as that includes a microprocessor, can be incorporated into the control electronics. The microprocessor controls the temperature and the amount of time at each temperature in the thermal cycle. The microprocessor can be programmed to conduct the appropriate thermal cycle for each type of sample material.

The means for attaching the various components described above will now be described. It is important that the means for attaching the various components does not result in significant heat transfer away from the thermal block assembly to the outside of the components. Any heat transfer which occurs from the thermal block assembly should occur through the thermal block plate, thermal interface elements, solid state heaters and heat sink in order to maximize temperature uniformity. These elements are designed to have uniform heating and cooling characteristics so that no one area of the thermal block plate will be cooled any faster than another area. The attachment fasteners must be provided in order to attach the thermal block plate 22, the thermal interface elements, the spacer bracket 46, the solid state heaters 40, and heat sink base 34. The attachment fasteners have been designed to minimize the heat transfer that occurs through the attachment fasteners.

As best shown in FIGS. 20 and 21, the flexible heating cover assembly 200 of the present invention includes a cover assembly skirt 250, a resistive heater 300, a heater backing plate 350, a spring strip 400, a spring retainer plate 450, a stiff support plate 500, and a plurality of heater slides 550. The aforementioned components engage each other to form the flexible heating cover assembly 200. A detailed discussion of each of these components will follow.

The flexible heating cover assembly 200 provides enhanced functions including the flexibility of the cover assembly and the force distribution. In addition, the flexible heating cover assembly 200 enables the resistive heater 300 to float in a vertical direction, so that the resistive heater 300 has some freedom of movement vertically which leads to a more uniform thermal contact and force distribution and more accurate and consistent results. The flexible heating cover assembly 200 provides thermal insulation for the upper portion of the sample tubes 140 and the sample caps 146.

The flexible heating cover assembly 200 engages a thermal system base 15 by a plurality of mechanical interfaces. The mechanical interfaces would be present in both the flexible heating cover assembly 200 and the thermal system base 15 and enable the functionality of this flexible heater cover assembly 200 when used in combination with the thermal system base 15. The mechanical interfaces allow a force connection to be made between the thermal system base 15 and the flexible heating cover assembly 200 to hold those two systems together. The force of the samples wells (and the reaction of that force in the flexible heating cover assembly 200) needs to imparted into the resistive heater 300 and further transferred into the sample tubes 140 and the sample caps 146. The force of the sample tubes 140 can vary depending on the number of sample wells and the contents of the sample tubes 140. The flexible heating cover assembly of the present invention is designed to provide a force of between about 10 grams to about 30 grams, per well, into the sample containers. The force distribution system is designed such that only about 10 grams of force, per well, are applied to low stiffness, low thermal mass sample container formats (i.e., single tubes or strip tubes of 8). For higher stiffness, higher thermal mass sample container formats (i.e., 96 well plates), the force distribution system is designed to provide up to about 30 grams of force, per well. The mechanical interfaces of the flexible heating cover assembly 200 also promote an insulating environment around an upper portion of the sample tubes 140 and the sample caps 146. Thus, the mechanical interfaces not only provide a physical barrier between the flexible heating cover assembly 200 and the thermal system base 15, the mechanical interfaces also transfer force between the force the flexible heating cover assembly 200 and the thermal system base 15.

The mechanical interfaces also allow the flexible heating cover assembly 200 to be located in a preferred position about the thermal system base 15 such that a favorable ambient environment is maintained around the portion of the sample tubes which extends above the thermal system base 15. The mechanical interfaces help control the location flexible heating cover assembly 200 vertically with respect to the thermal system base 15. Proper vertical positioning of the flexible heating cover assembly 200 with respect to the thermal system base 15 allows for maintenance and support of force imparted by the sample tubes 140 and the sample caps 146. If the vertical position of the flexible heating cover assembly 200 with respect to the thermal system base 15 were changed, that force could increase or decrease causing inefficient performance if the force gets too high or too low.

It is also important to maintain a favorable ambient environment around the portion of the sample tubes 140 which extends above the thermal system base 15. During thermal cycling in quantitative PCR and similar procedures, the fluid inside the sample tubes 140 is repeatedly heated and cooled over a wide temperature range, for example from about 50° C. to about 95° C. If the sample tubes caps 146 are not heated adequately at various times during the thermal cycling, vapor may condense in the upper walls of the sample tubes 140 and on the inside surface of the sample tubes caps 146. The vapor and possible condensation of the vapor, if it is not a consistent variable in the user's experiment on a tube-to-tube basis, can affect the fluorescence readings and impact the performance of the instrument and the consistency of data. Thus, it is desirable to limit vapor formation. The resistive heater 300 above the sample tube caps 146 limits the vapor and condensation formation by maintaining the temperature around the sample tube caps 146 above the dew point temperature to limit the vapor creation in the air above the liquid sample that can distort the fluorescent readings. The benefits of the resistive heater 300 are enhanced if there is a favorable ambient environment in many aspects. First, the ambient environment has a temperature closer to the temperature range in the resistive heater 300 (i.e., about 85° C. to about 110° C.). So if the temperature around the resistive heater 300 is closer to that range, as opposed to the ambient temperature inside the instrument (i.e., about 25° C. to about 32° C.), then that elevated ambient temperature is one aspect that creates a favorable ambient environment. Another aspect of the favorable ambient environment is a physical structure around the resistive heater 300 and around the upper portion of the sample tubes 140 and the sample tube caps 146 to minimize the free convective airflow and the resulting heat transfer from convection. The airflow can be impacted by a numerous factors. First, fans external to the flexible heater cover assembly 200 pull air through the instrument, and the fans can create moving air inside the instrument. The impact of moving air inside the instrument from the fans should be limited. Also, the impact of the movement of air from moving the entire thermal system in one axis to accomplish the acquisition of the fluorescence data should be limited. As the entire thermal system is moved in one axis to acquire fluorescence data, that movement is also creating higher air movements. The flexible heating cover assembly 200 of the present invention helps to minimize the convective problems where heat is lost to the ambient environment. Thus, the elevated ambient temperature and the lower convective coefficient and lower convective heat transfer promote the function of the resistive heater 300.

The thermal system base 15 should have certain characteristics to optimize the benefits of the flexible heating cover assembly 200 of the present invention. First, certain mechanical interfaces of the thermal system base 15 help promote or apply the reactive force that is needed to maintain the downward force of the sample tubes 140 so that the flexible heating cover assembly 200 can impart that force into the sample tubes 140 and sample tube caps 146. As discussed above, the thermal system base 15 has a rectangular window frame component that has a flat surface on at least two of the four perimeter sides. The frame component provides vertical position, helps control the ambient environment acting as an insulator, and structurally provides a base to clamp the flexible heating cover assembly 200 onto, and provide position registration. The thermal system base 15 also has a pivoting clamp assembly with four contact points that interface with four points in the flexible heating cover assembly 200. The four contact points are preferably located near the front corner and the rear corner on a left side and a right side of the thermal system base 15. The four contact points also interface with the pivoting clamping assembly and with the flexible heating cover assembly 200 to create a force connection that transfers force between the thermal system base 15 and the flexible heating cover assembly 200. In a preferred embodiment of the present invention, the clamp assembly is driven by an electric motor and activated by a software control. There are also some springs in that assembly and some mechanical parts that pivot back and forth. The three main aspects of the mechanical requirements of the thermal system base 15 that optimize the benefits of the flexible heating cover assembly 200 of the present invention are the preferred position (primarily vertical), the favorable environment, and then the force application.

The flexible heating cover assembly 200 of the present invention is designed to operate with an optical scanning or optical data collection equipment for quantitative PCR. Numerous features of the flexible heating cover assembly 200 are designed to optimize its use with optical scanning or optical data collection equipment. First, the plurality of sample well holes in the components of the flexible heating cover assembly 200 create an optical channel in which the fluorescent dye molecule that is attached to the DNA or that is not attached to the DNA can be excited. The plurality of optical channels provide an optical avenue for exciting and collecting the optical data. The plurality of optical channels also can transmit the emitted fluorescent signal from the fluorescent dye in the sample to certain optical components to collect optical data on the samples. Light travels down the optical channels, hits the fluid and any dye surrounding or attached to the DNA in the sample, and the emitted light is bounced back up the optical channels and is collected with various optical components. Second, optical data should not only be collected from each sample well, but the sensitivity (or the signal-to-noise performance) is also important because with DNA and the fluorescent molecules that are attached to or around the DNA, there is a limited amount of physical material and dye. Therefore, the light that is emitted is very minimal, and so sensitivity is important to try to pick up as much of this low-level light as possible. Therefore, the flexible heating cover assembly 200 is thin to assist with optical sensitivity in the data collection and the optical performance. Third, because optical scanning is used to collect the data, a plurality of stiffening ribs in the stiff support plate 500 in the flexible heating cover assembly 200 provide stiffness for the flexible heating cover assembly 200. The stiffening ribs are arranged to promote scanning between the stiffening ribs. For example, optical equipment that scans at a mostly constant velocity can be located between the stiffening ribs that are in the stiff support plate 500. In a preferred embodiment of the present invention, the flexible heating cover assembly 200 operates with an optical scanning or optical data collection means located above the flexible heating cover assembly 200. In other embodiments of the present invention, optical scanning from areas other than above the flexible heating cover assembly 200 could be employed, but there may be cost factors and/or optical complexities which should be considered.

The flexible heating cover assembly 200 of the present invention offers numerous performance advantages over the prior art including, but not limited to, the following: (1) the distribution of heat in the resistive heater 300; (2) the flexibility of the resistive heater 300; (3) the vertical movement of the resistive heater 300 within the flexible heating cover assembly 200; (4) the stiffness of certain components (i.e., the spring retainer plate 450, the stiff support plate 500); and (5) the configuration of the spring strips 400. Other advantages of the flexible heating cover assembly 200 of the present invention are discussed throughout the specification.

FIGS. 20 and 21 show the vertical distribution of the various components of the flexible heating cover assembly 200 as follows from top to bottom: (1) the stiff support plate 500; (2) the base of the spring strips 400 on a bottom surface of the spring retainer plate 450; (3) the heater backing plate 350; (4) the resistive heater 300; (5) the cover assembly skirt 250; and (6) the sample caps 146 of the sample tubes 140. Each of the components of the flexible heating cover assembly 200 will now be discussed.

As shown in FIGS. 20 and 21, the cover assembly skirt 250 includes a plurality of end caps 260 with a plurality of side support bars 270. In a preferred embodiment of the present invention, there are two end caps 260 and two side support bars 270. In other embodiments of the present invention, any number of the end caps 260 and the side support bars 270 may be used. The side support bars 270 engage each of the end caps 260 so the combination of end caps 260 and the side support bars 270 form a perimeter enclosure for the flexible heating cover assembly 200. The various components of the cover assembly skirt 250 create a favorable ambient environment due to their shape and composition of thermally insulating materials. A shoulder in the stiff support plate 500 assists in aligning and fastening the various components of the cover assembly skirt 250 with an adjacent shoulder that would allow for some alignment variation. Mechanical fasteners attach the various components of the cover assembly skirt 250. Those skilled in the art will recognize that other combinations of mechanical fasteners are within the spirit and scope of the invention.

In a preferred embodiment of the present invention, the various components of the cover assembly skirt 250 are composed of polycarbonate (PC) (common trade names include lexan). Those skilled in the art will recognize that other materials with similar characteristics could be used within the spirit and scope of the present invention including, but are not limited to, acetal (common trade names include delrin), polyetherimide (PEI) (common trade names include ultem), polyamide (common trade names include zytel and nylon), and similar materials.

The stiff support plate 500 also contains other mechanical features which can be used to attach the cover assembly skirt components 250 to achieve an ambient environment around the upper portion of the sample tubes 140 and sample tubes caps 146 which is favorable. The stiff support plate 500 and various cover assembly skirt components 250 minimize the convective heat loss and minimize any convective air flow disruptions which could degrade the target temperature of the flexible heater assembly 200 or the thermal system base 15.

FIGS. 22–26 show varying views of the resistive heater 300 of the flexible heater cover assembly of the present invention. The resistive heater 300 includes a heater insulation 302, a thermistor 304, and a plurality of heater pads 340. In a preferred embodiment of the present invention, the heater insulation 302 is generally rectangular in shape and has slanted corners 308, a plurality of notched sections 310, a plurality of sample well holes 312. In other embodiments of the present invention, other shapes for the heater insulation 302 could be used (i.e., oval, square, and similar shapes) and any number of sample well holes 312 are present.

Figure 22:
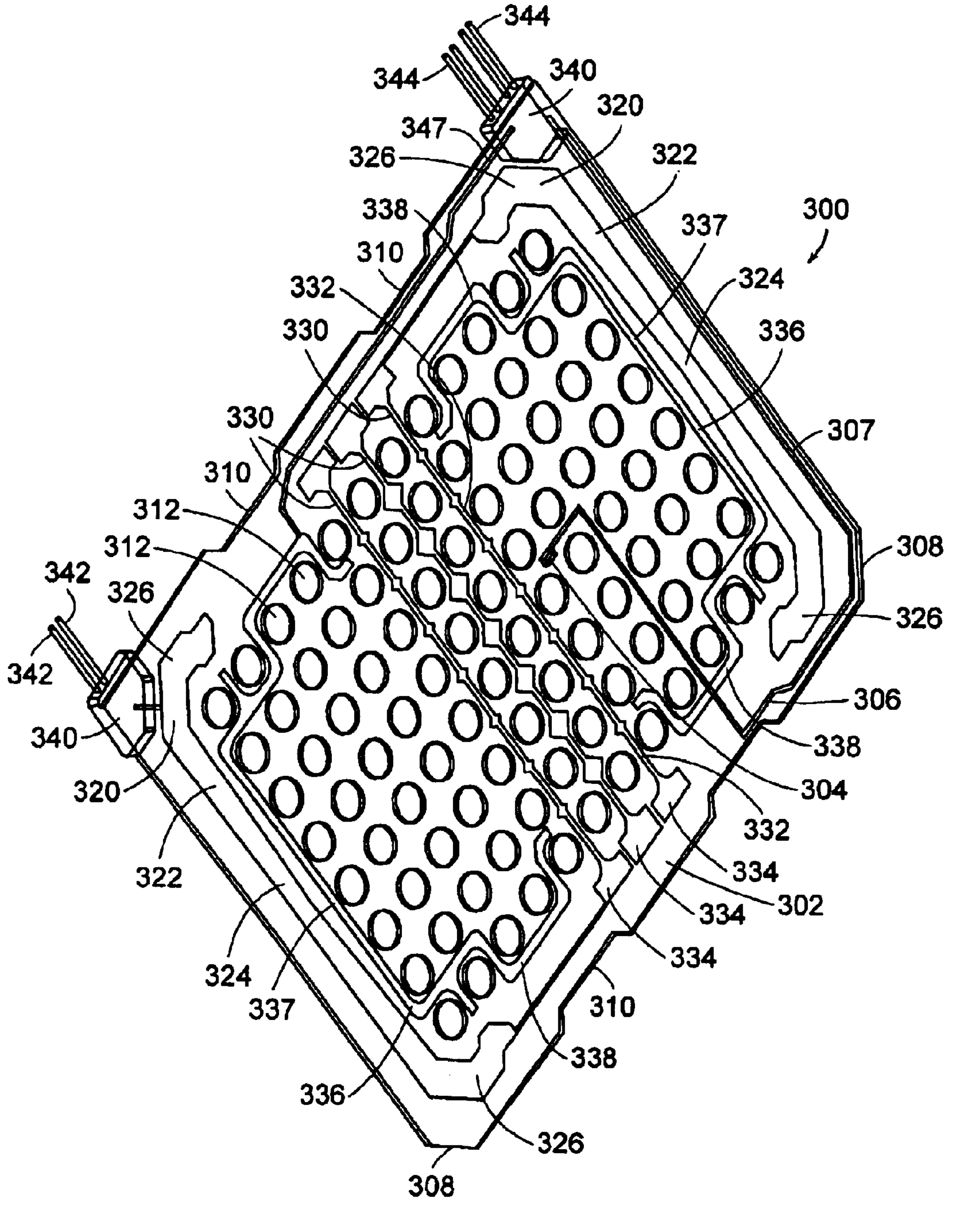
FIG. 22 is a perspective view of a resistive heater of a flexible heating cover assembly of the present invention showing a layout of a plurality of heater element areas.
Figure 23:
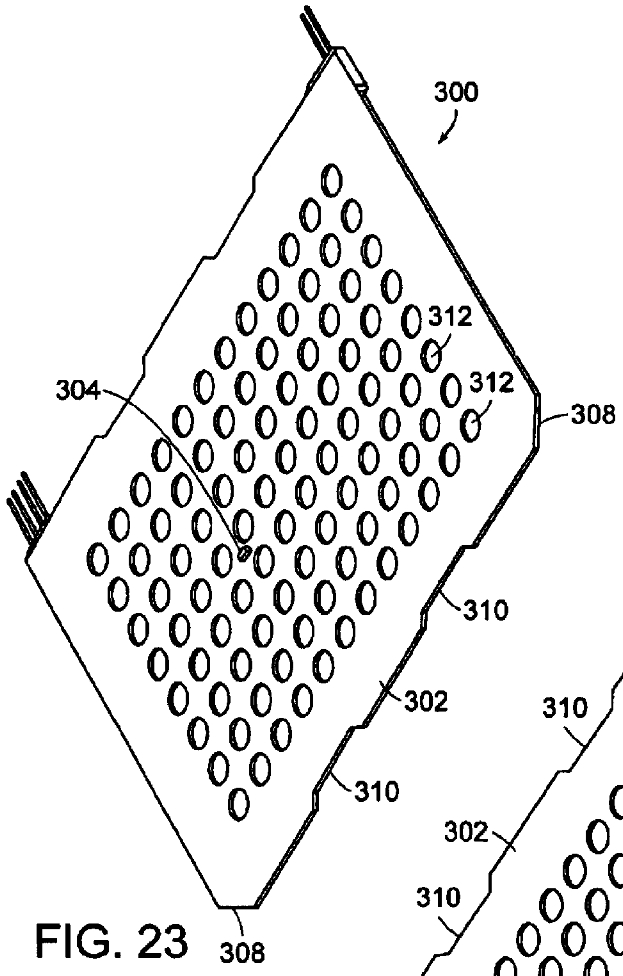
FIG. 23 is a top perspective view of a resistive heater of a flexible heating cover assembly of the present invention showing a thermistor.
Figure 24:
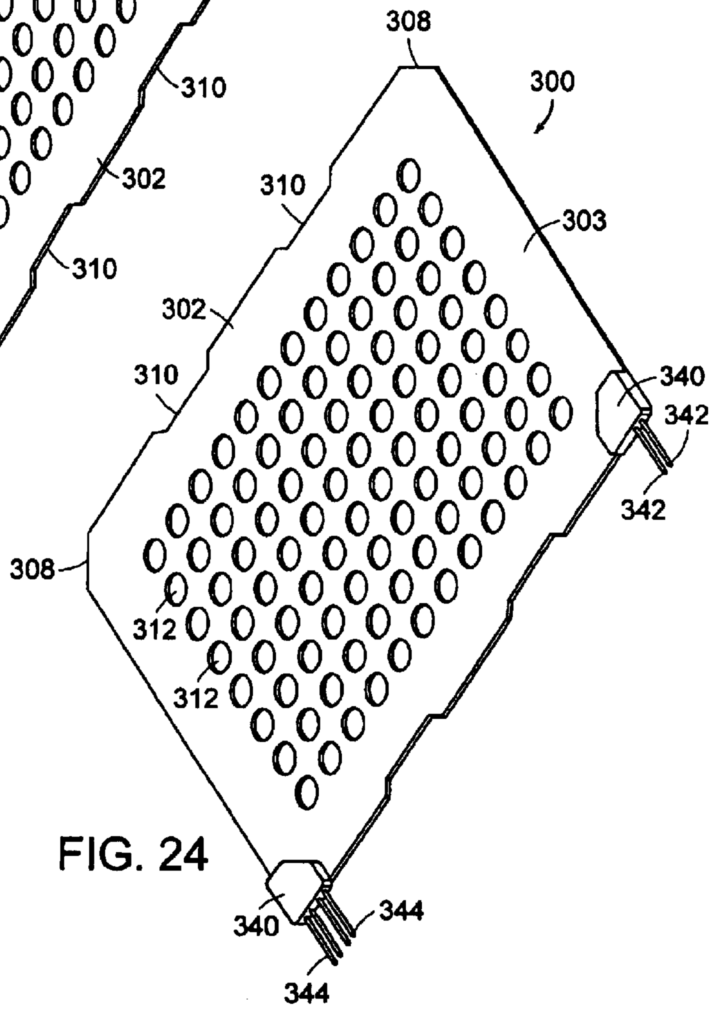
FIG. 24 is a bottom perspective view of a resistive heater of a flexible heating cover assembly of the present invention showing a plurality of insulating pads.
Figure 25:
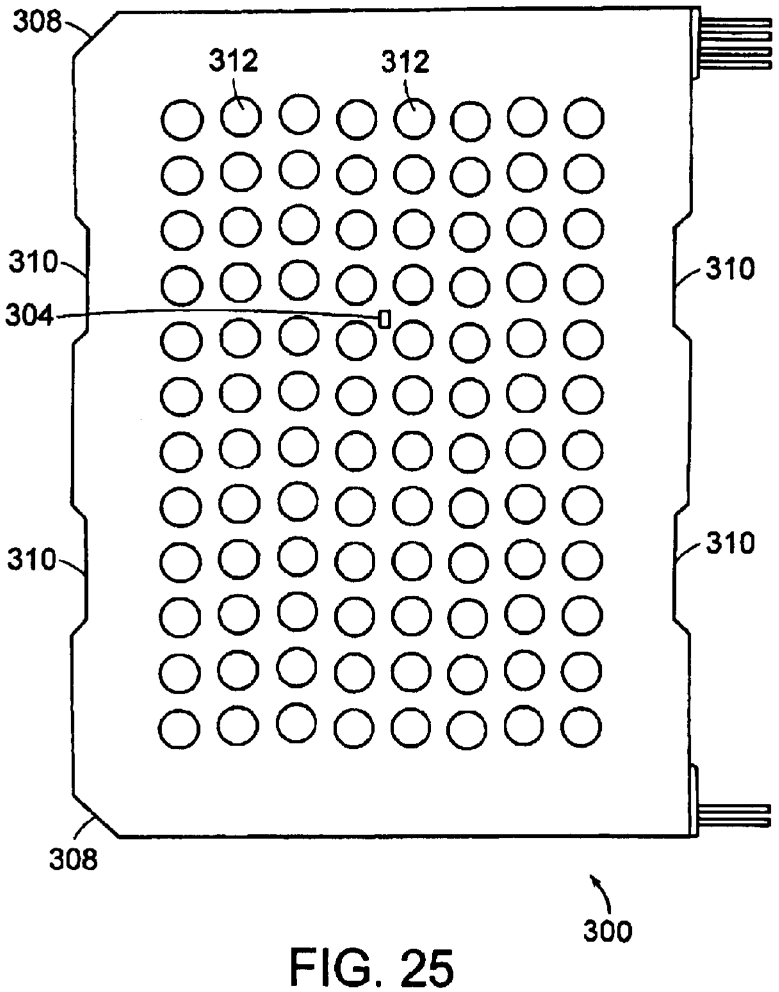
FIG. 25 is a top view of a resistive heater of a flexible heating cover assembly of the present invention showing a thermistor.
Figure 26:
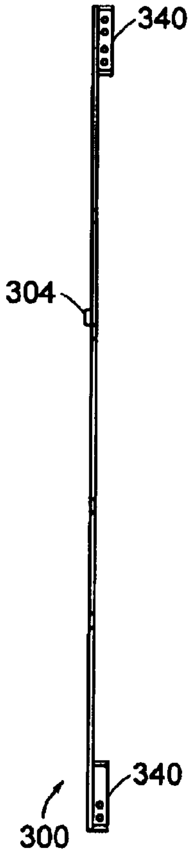
FIG. 26 is a side view of a resistive heater of a flexible heating cover assembly of the present invention.

As best shown in FIG. 22, the resistive heater 300 also includes a plurality of outer heater element areas 320 and a plurality of central heater element areas 330. The resistive heater 300 produces a non-uniform heat distribution along the surface exposed to the sample tubes caps 146 in at least two dimensions (the x dimension and y dimension). In a preferred embodiment of the present invention, the resistive heater 300 generates electrical heat in five primary areas across the heater insulation 302 including two outer heater element areas 320 and three central heater element areas 330. One outer heater element area 320 is located toward each end of the heater insulation 302. In a preferred embodiment of the present invention, the outer heater element area 320 is C-shaped and located along the outer edge of the sample well holes 312. The C-shape of the outer heater element area 320 provides superior heat balance to achieve an optimized thermal uniformity in the temperature range commonly used for the PCR process (i.e., about 37° C. to about 95° C.). The C-shape of the outer heater element area 320 includes a long portion 322 having a tapered portion 324 and curved end portions 326. At each end of the heater insulation 302, there are eight sample wells along the long portion 322 of the C-shape. The tapered portion 324 is located adjacent rows four and five of the eight sample well rows. The tapered portion 324 is thinner than the other long portions 322 of the C-shape. The curved end portion 326 of the C-shape are wider than the long portion 322 of the C-shape. The C-shape of the outer heater element area 320 including the tapered portion 324 which provides greater thermal uniformity and a favorable thermal distribution. In other embodiments of the present invention, any number of outer heater element areas could be used (i.e., one outer heater element area, three outer heater element areas, four or more outer heater element areas). In other embodiments of the present invention, the outer heater element areas can have many different shapes including, but not limited to, columns, spirals, curves, zigzags or similar shapes.

In a preferred embodiment of the present invention, three central heater element areas 330 are used. The central heater element areas 330 have an elongated portion 332 and an end cap section 334 at each end. The end cap section 334 of the central heater element area 330 is wider than the elongated portion 332 and the end cap section 334 is located past the sample well holes 312 toward the outer edge of the heater insulation 302. In a preferred embodiment of the present invention, the central heater element areas 330 are column shaped and extend across the heater insulation 302 and are generally parallel to each other. In other embodiments of the present invention, the central heater element areas 330 can have many different shapes including, but not limited to, spirals, curves, zigzags or similar shapes. In other embodiments of the present invention, any number of central heater element areas 330 could be used (i.e., one central heater element area, two central heater element areas, four or more central heater element areas).

The central heater element areas 330 improve the heating ramp rate of the resistive heater 300 from about 0.15° C./sec. to about 0.30° C./sec. The faster response for the resistive heater 300 with the central heater element areas 330 allows the resistive heater 300 to be controlled at a variety of temperatures during the PCR process such that the quality of quantitative PCR data is more accurate. During denaturing temperatures of the PCR process (about 95° C.), the resistive heater 300 can be controlled to a higher temperature range (about 100–110° C.). During the annealing or extension temperatures of the PCR process (about 37–75° C.), the resistive heater 300 can be controlled to a lower temperature range (about 55–90° C.). The fast response heater temperature control for the resistive heater 300 with the central heater element areas 330 provides superior thermal uniformity over constant temperature controlled heater scenarios. The ramp rate of the resistive heater 300 is sufficient to minimize any condensation which could form inside the sample tube cap surface during thermal cycling.

The location and distribution of the heating areas in the resistive heater 300 have been optimized to provide improved quantitative PCR data. The optimized performance is gained when used with a thermal system base 15 and an optical scanning configuration as described herein. A heat balance exists between the flexible heating cover assembly 200 and the thermal system base 15 creates a more uniform temperature distribution in all sample tubes 140. The heat balance in the flexible heating cover assembly 200 of the present invention is optimized for the heat distribution that is present in the heating and cooling aspects of the thermal system base 15 discussed above which is preferred to be a copper block assembly. The flexible heating cover assembly 200 and the thermal system base 15 balance each other, and if a different thermal system base has a different thermal distribution, the performance of the flexible heating cover assembly 200 may not be optimized. With a different thermal system base 15 and/or optical scanning methods, it may be necessary to adjust the hardware or control software to obtain optimized thermal performance.

The resistive heater 300 not only has central heater element areas 330, but other heating element areas to improve the performance of the resistive heater 300. The resistive heater 300 contains a plurality of heat carrier circuits 336 which are not electrically connected to the heater power source, but act to increase the thermal conductivity of the resistive heater 300. The plurality of heat carrier circuits 336 help to optimize the thermal uniformity for the thermal system base 15. In the resistive heater 300, the presence of the heat carrier circuits 336 improves that thermal connectivity across the heater in the X and Y directions. Placing the plurality of heat carrier circuits 336 that are not electrically connected in various areas of the heater insulation 302 increases the speed of the heat movement through the heater insulation 302 in the X and Y directions and improves performance of the entire system.

As shown in FIG. 22, the heat carrier circuits 336 are generally C-shaped and are located inside the C-shaped outer heater element area 320. In a preferred embodiment of the present invention, two heat carrier circuits 336 are used. One heat carrier circuit 336 is located on the left side of the heater insulation 302 and another heat carrier circuit 336 is located on the right side of the heater insulation 302. Each heat carrier circuit 336 includes an elongated portion 337 and a plurality of legs 338. The legs 338 of the heat carrier circuits 336 are longer than the curved end portions 326 of the C-shaped outer heater element area 320. In addition, the heat carrier circuits 336 are generally thinner than the C-shaped outer heater element areas 320 located adjacent to the heat carrier circuits 336. The heat carrier circuit 336 is preferably composed of a conductive metallic material although those skilled in the art will recognize that the heat carrier circuit 336 can be composed of any conductive material. In other embodiments of the present invention, any number of heat carrier circuits 336 could be used (i.e., one heat carrier circuit, three heat carrier circuits, four or more heat carrier circuits).

In a preferred embodiment of the present invention, both heat carrier circuit 336 help speed transfer through the heater insulation 302. The heat carrier circuit 336 located on the right side of the heater insulation 302 is not connected to either the heater power source or any lead wires 344. The heat carrier circuit 336 located on the left side of the heater insulation 302 is electrically connected to two lead wires which allows the heat carrier circuit 336 located on the left side of the heater insulation 302 to act as a temperature-sensing device because it is electrically connected to lead wires (but not to the heater power source). As the heater temperature changes, the resistance of the left side heat carrier circuit 336 changes in a predictable manner. The resistance of the left side heat carrier circuit 336 can be monitored through the lead wires 344, and used to provide a control means to the heater power source for heater temperature control.

The resistive heater 300 also contains the thermistor 304 and a thermistor lead circuit 306. The thermistor 304 is an electronic component whose resistance changes with temperature. The voltage and current of the thermistor 304 can be measured as the temperature changes. The thermistor 304 is located toward the center portion of the heater insulation 302. The thermistor lead circuit 306 extends from the thermistor 304 and uses a trace routing 307 to connect the thermistor 304 to a wire exit area near the plurality of heating pads 340. The thermistor lead circuit 306 follows a path from the thermistor 304 along the outer edge of the heater insulation 302 to the wire exit area where the thermistor lead circuit 306 connects to two of the four lead wires 344. The thermistor lead circuit 306 has a small profile which is advantageous because it functions without bulky wires that could disrupt the heater-to-sample tube cap thermal interface and/or the thermal distribution along the heater insulation 302.

The location of the thermistor 304 also provides advantages over the prior art. The response the resistive heater is driven by the location of the thermistor 304 on the heater insulation 302. Prior art heater assemblies located the thermistor in the corner of the heater insulation near the wire exit area because then the thermistor lead circuit is short and simple. However, because the heat distribution is greater near the corners, sides, and, to some extent, the perimeter of the heater insulation 302 if the thermistor is located the corner, the control of the resistive heater 300 is driven primarily by the corner temperature. This can cause a time-lag problem with the control and performance of the center portion of the heater insulation that has a smaller heat distribution than the corners of the heater insulation. The time-lag problem results in the center portion of the heater insulation lagging behind the control of the corner and perimeter portions of art of the heater insulation. The flexible heating cover assembly 200 of the present invention eliminates much of the time-lag problem by locating the thermistor 304 toward the center portion of the heater insulation 302. The location of the thermistor 304 near the center of the resistive heater 300 provides greater control of the vapor and condensation environment. The dew-point temperature is controlled by the target temperature of the sample block, the ambient temp around the sample tubes 140, the pressure inside the sample tubes 140, and the fluid volume inside the sample tubes 140. Thus, locating the thermistor 304 toward the center portion of the heater insulation 302 improves the performance of the resistive heater 300.

The design characteristics and dimensions of the resistive heater 300 also promote performance. The heater insulation 302 refers to the material surrounding the heater element areas. The heater insulation 302 also accounts for almost the entire thickness of a the resistive heater 300 because the heater insulation 302 is usually much thicker than the heater element areas. The heater insulation 302 is preferably composed of silicone rubber, which provides insulation for the resistive heater 300. The silicone rubber surface is relatively soft to promote flexibility of the resistive heater 300 allowing the resistive heater 300 to contact all the sample tube caps 146 to promote conductive heat transfer. The silicone rubber material also provides a superior mechanical connection with the heater backing plate which will be discussed below. Other materials that could be used for the heater insulation 302 include, but are not limited to, polyimide (P1) (common trade names include kapton), mica, polyester, nomex, and other similar materials. Kapton is a common insulating material that used in various applications including flex circuits, flexible heaters and resistive heaters. Kapton is a very good electrical insulator and a good thermal insulator. Mica is another insulating material that is used in heaters for other performance reasons. Those skilled in the art will recognize that other insulating materials known in the art would be within the spirit and scope of the present invention.

The resistive heater 300 should be thick enough to generate a favorable temperature gradient to promote optimized thermal uniformity with the thermal system base 15, yet thin enough to allow rapid heating and cooling during thermal cycling. The preferred thickness of the heater insulation 302 is 0.026 inches which is relatively thin, although those skilled in the art will recognize that other thicknesses would be within the spirit and scope of the present invention. The weight of the resistive heater 300 is kept lower because the heater insulation 302 contains the plurality of sample well holes 312 which provide optical transmission capability and are sized to permit emitted radiation to pass through consistent with an optical scanning from above configuration.

As shown in FIG. 22, the resistive heater 300 also includes a plurality of heating pads 340 with a plurality of power source wires 342 and a plurality of lead wires 344 extending from the heating pads 340. In a preferred embodiment of the present invention, two heating pads 340 are located at each of the rear corners of a bottom side 303 of the heater insulation 302. The heater pads 340 have a larger thermal mass and tend to absorb heat which takes away heat that could otherwise be transferred in the heater insulation 302. The heating pads 340 provide a connection area between the lead wires and the other components of the resistive heater 300.

The heating pad attached to the left side of the heater insulation 302 has two power source wires 342 that are connected to the heater power source so a voltage is carried through the two power source wires 342. The power source wires 342 are connected to the heater power source and extend into the heater pad 340 where they connect through trace routings 347 with the outer heater element areas 320 and the plurality of central heater element areas 330. In a preferred embodiment of the present invention, the power source wires 342 connect to the heater power source for and also connect to the C-shaped outer heater element area 320 on the left side of the heater insulation 302 which is connected to the three central heater element areas 330 which is connected to C-shaped outer heater element area 320 on the right side of the heater insulation 302. Thus, two power source wires 342 supply electrical power to the two outer heater element areas 320 and the three central heater element areas 330 which are connected in one circuit.

The heating pad 340 attached to the right side of the heater insulation 302 has four lead wires 344 that are connected to the heating pad 340. Two of the lead wires 344 are electrically connected to the thermistor 304 through trace routings 307 and then the other two lead wires 344 are connected to the heat carrier circuit 336 located on the left side of the heater insulation 302 to increase the speed of heat transfer.

Figure 27:
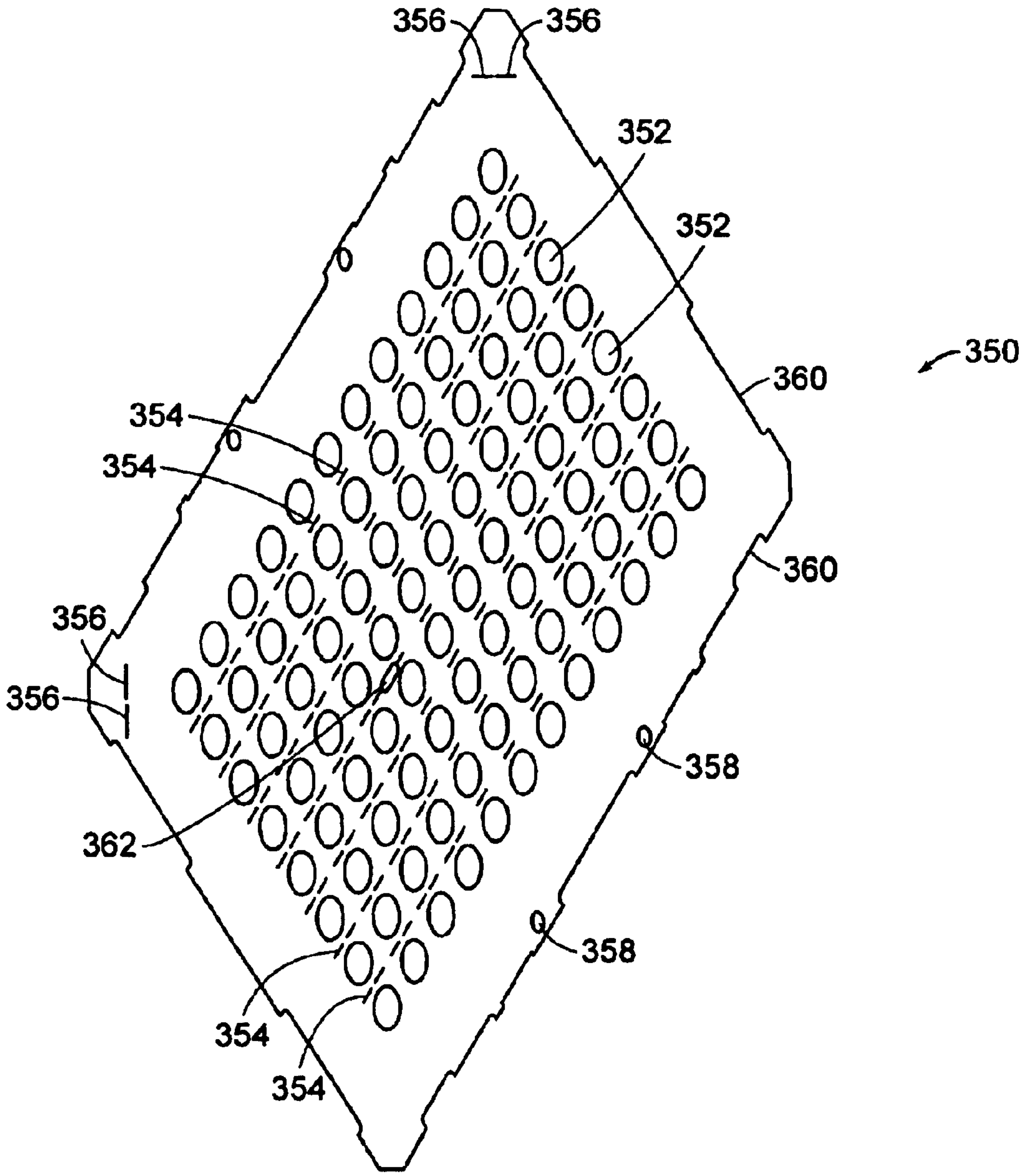
FIG. 27 is a perspective view of a heater backing plate of a flexible heating cover assembly of the present invention.
Figure 28:
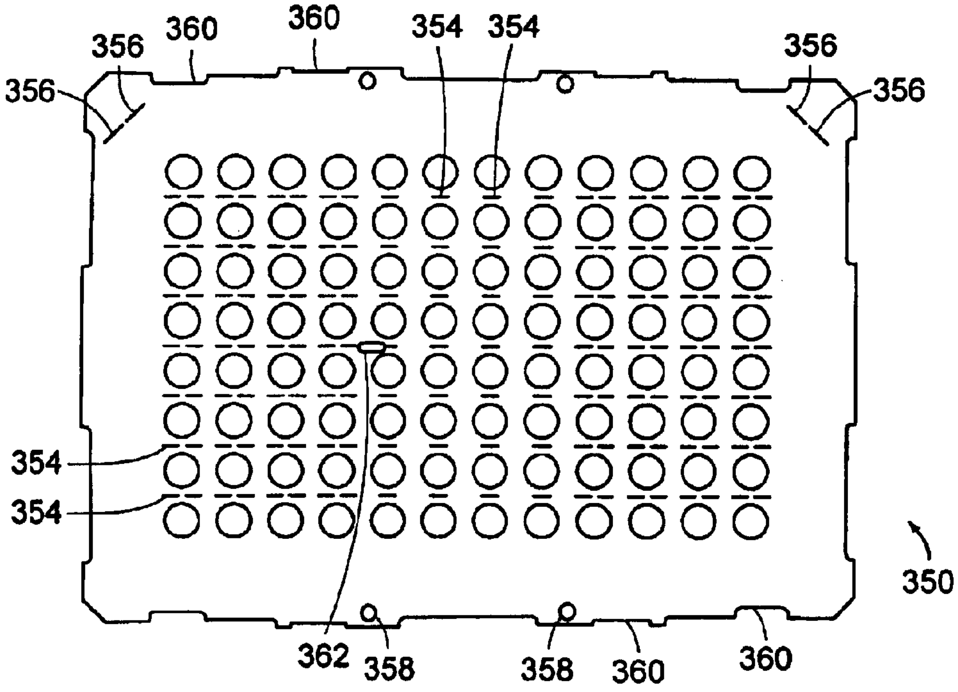
FIG. 28 is a top view of a heater backing plate of a flexible heating cover assembly of the present invention.
Figure 29:
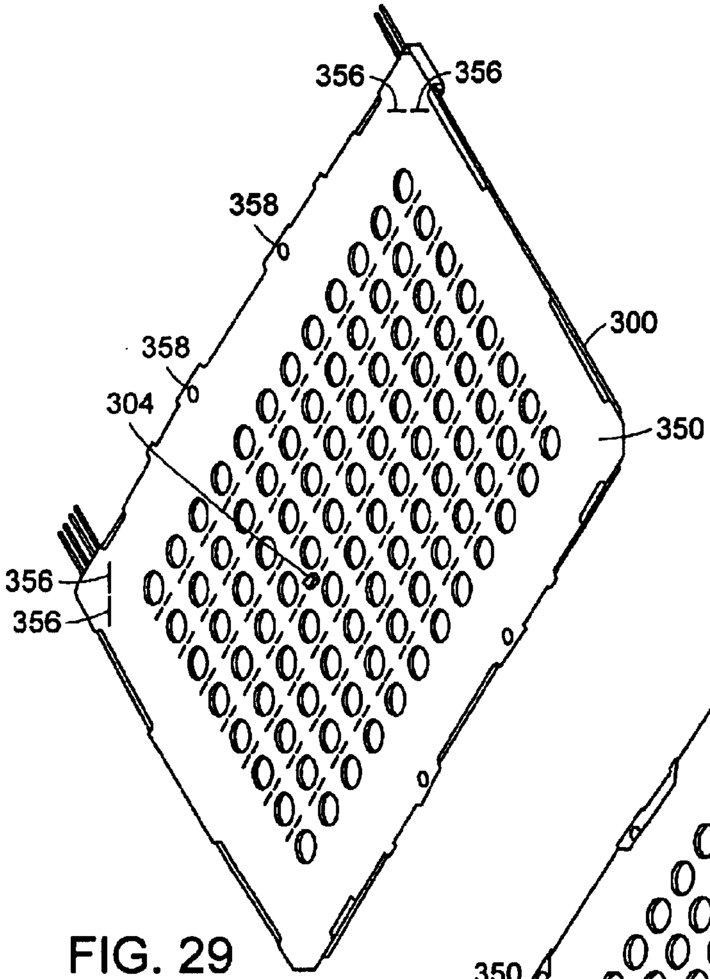
FIG. 29 is a top perspective view of a resistive heater engaging a heater backing plate of a flexible heating cover assembly of the present invention.
Figure 30:
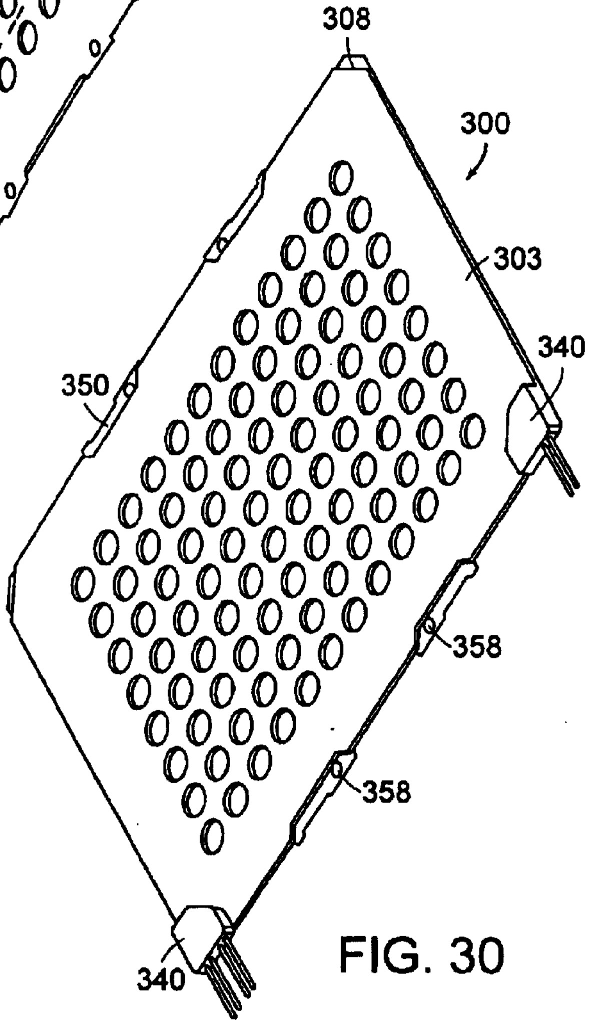
FIG. 30 is a bottom perspective view of a resistive heater engaging a heater backing plate of a flexible heating cover assembly of the present invention.
Figure 31:
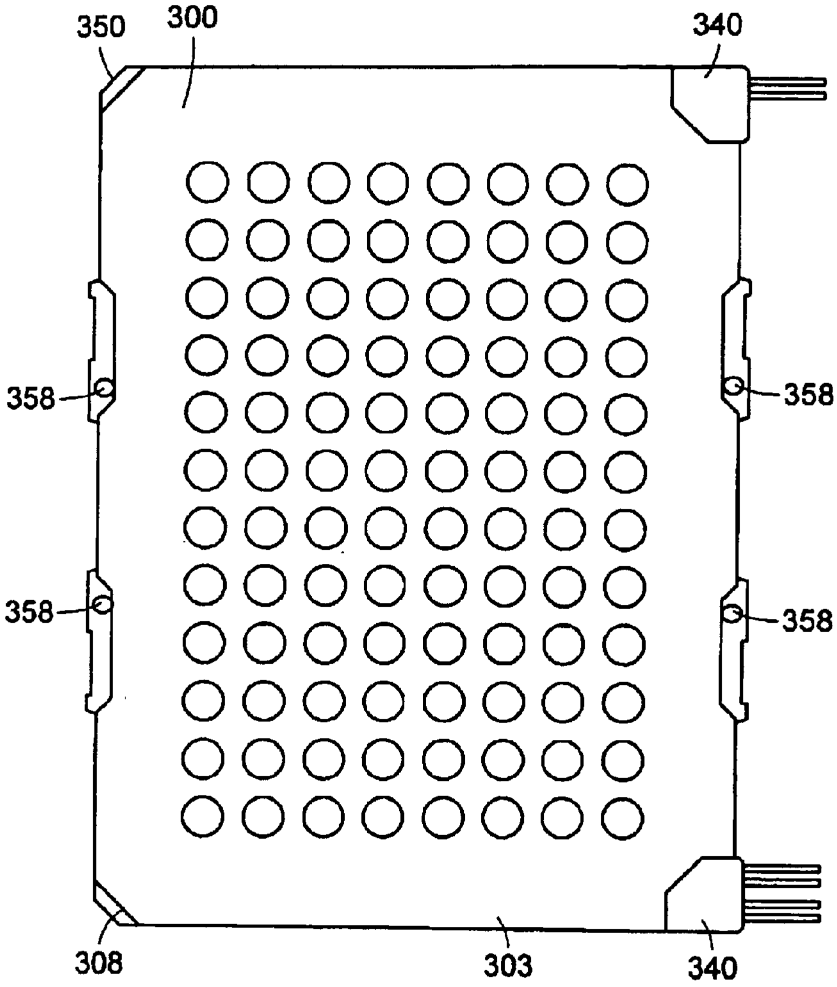
FIG. 31 is a bottom view of a resistive heater engaging a heater backing plate of a flexible heating cover assembly of the present invention.
Figure 32:
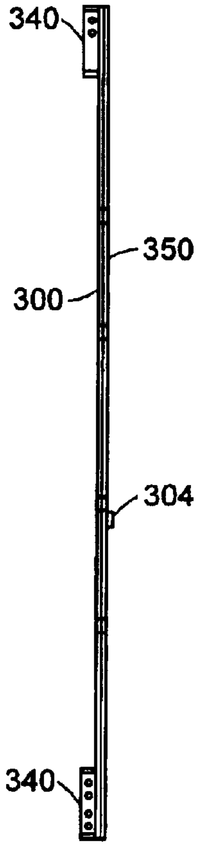
FIG. 32 is a side view of a resistive heater engaging a heater backing plate of a flexible heating cover assembly of the present invention.

As shown in FIGS. 27 and 28, the flexible heater cover assembly also includes the heater backing plate 350. The heater backing plate 350 is thin, flexible, and thermally conductive. The heater backing plate 350 is similar in size and shape to the resistive heater 300. The preferred thickness of the heater backing plate 350 is 0.018 inches, although those skilled in the art will recognize that other thicknesses would be within the spirit and scope of the present invention. The heater backing plate 350 also contains a plurality of sample well holes 352, a plurality of narrow slots 354, a plurality of corner slots 356, a plurality of securing holes 358, a plurality guide cut-outs 360, and a thermistor cut-out 362.

The heater backing plate 350 has a plurality of sample well holes 352 designed to allow the sample tubes 140 to fit in the sample well holes 352. In a preferred embodiment of the present invention, there are 96 sample wells and 96 corresponding sample well holes 352 in the heater backing plate 350. The weight of the heater backing plate 350 is kept lower because the heater backing plate 350 contains the plurality of sample well holes 352 which provide optical transmission capability and are sized to permit emitted radiation to pass through consistent with an optical scanning from above configuration. As discussed above, other numbers of tubes 140 and sample well holes 352 are within the spirit and scope of the present invention.

As shown in FIG. 28, the plurality of narrow slots 354 throughout the heater backing plate 350 promote the flexibility of the plate 350 and direct heat transfer on the plate 350. The slots 354 are mainly in the horizontal X direction between the plurality of sample well holes 352. The slots 354 oriented in generally parallel rows between each row of sample well holes 352. A reasons for this orientation of the slots 354 is that the main heat flow in the heater backing plate 350 is in the horizontal X direction both toward the center, and away from the center toward the sides. Although there is some heat flow in the vertical Y direction, the primary heat flow in the heater backing plate 350 is in the horizontal direction from left to right or right to left. The slots 354 are oriented to minimize the retardation of that heat flow in at least one direction. The slots 354 promote flexibility while not disrupting the ability of the heat to flow freely in the heater backing plate 350.

The number and configuration of the slots 354 is designed to facilitate heat flow in the heater backing plate 350 and to not interfere with the heat emanating from the central heater element areas 330. The slots 354 are arranged in either a single slot or a double slot formation throughout the heater backing plate 350 with the single slots 354 located toward the center of the plate 350, and the double slots 354 are located toward the outer edges of the plate 350. The single slot 354 configuration toward the center of the heater backing plate 350 is arranged so that the central heater element areas 330 do not cross over a slot. Thus, the central heater element areas 330 are completely covered by the a solid metallic material of the heater backing plate 350. If the central heater element areas 330 would cross over the slot 354, a local temperature differential would be created. The local temperature differential creates a thermal stress that decreases the reliability of the resistive heater 300 and could even cause failure of the resistive heater 300. The double slots 354 toward the outer edges of the heater backing plate 350 promote heat flow in the Y direction and minimize the thermal barrier between sample well holes 352 in the Y direction. The number and configuration of the slots 354 is designed to minimize the disruption of conductive heat flow through the heater backing plate 350.

Each back corner of the heater backing plate 350 contains a plurality of corner slots 356 that are diagonally oriented to create a heat barrier. When the heater backing plate 350 is attached to the resistive heater 300, the heater pads 340 of the resistive heater 300 have a much larger thermal mass than the heater backing plate 350 which is thin. Thus, heat is drawn toward the corners of the heater backing plate 350 where the heater pads 340 with larger thermal mass are located. Further, the heater pads 340 tend to absorb heat which takes away heat that could otherwise heat the heater backing plate 350. The plurality of corner slots 356 create a heat barrier that diverts heat that would otherwise be drawn to the larger thermal mass of the heater pads 340 to other portions of the heater backing plate 350. Thus, the plurality of corner slots 356 assist in efficiently heating the plate 350 and minimize the disruption of conductive heat flow through the heater backing plate 350.

The heater backing plate 350 also contains the plurality of securing holes 358. A plurality of securing pins are placed in the securing holes 358 to insure that the resistive heater 300 and the attached heater backing plate 350 are retained at all times in the flexible heating cover assembly 200 during loading and unloading of the sample tubes 140. In a preferred embodiment of the present invention, four securing holes 358 and securing pins are used. Those skilled in the art will recognize that other number of securing holes 358 and securing pins would be within the spirit and scope of the present invention. The securing holes 358 in the heater backing plate 350 are larger than the pins so that the resistive heater 300 may move vertically about the pins without a large friction force. This vertical movement of the resistive heater 300 can accommodate the range of installed heights for various sample tubes 140 formats and various tolerances.

The heater backing plate 350 contains the plurality of guide cut-outs 360 that are used as a guide interface. In a preferred embodiment of the present invention, four guide cut-outs 360 are used. Those skilled in the art will recognize that other number of securing holes 358 and securing pins would be within the spirit and scope of the present invention. In addition, the heater backing plate 350 contains the thermistor cut-out 362 that permits the thermistor 304 to project through the heater backing plate 350 when the plate 350 is attached to the resistive heater 300. The thermistor cut-out 362 is slightly larger than the size of the thermistor 304 so not to interfere with temperature change readings from the thermistor 304.

The heater backing plate 350 should be thermally conductive so that the ramp rate of the resistive heater 300 is not degraded by the added thermal mass of the heater backing plate 350. Because the heater backing plate 350 should be thermally conductive, thin, and flexible, the heater backing plate 350 can be composed of a metallic material. In a preferred embodiment of the present invention, the heater backing plate 350 is composed of aluminum alloy 1100 with a temper designation of H12 or H14. Other aluminum alloys that could be used within the spirit and scope of the present invention include, but are not limited to, aluminum 6061-T6, aluminum 6063, aluminum 5032 and similar aluminum alloys. Those skilled in the art will recognize that other aluminum alloys known in the art would be within the spirit and scope of the present invention. In addition, any other thermally-conductive metal that is available a thin foil or a thin plate form could be used within the spirit and scope of the present invention. Other thermally-conducted metals that could be used include, but are not limited to, copper alloys, silver alloys, carbon steel, stainless steel and similar metals. Those skilled in the art will recognize that other metals and alloys known in the art would be within the spirit and scope of the present invention.

As shown in FIGS. 29–32, the bottom surface of the heater backing plate 350 is connected to the resistive heater 300 to provide protection and stability while promoting heat transfer. The heater backing plate 350 provides protection for the resistive heater 300 from handling damage and spring damage. The heater backing plate 350 acts as a heat carrier for the resistive heater 300 providing a certain thermal gradient across the resistive heater 300. The heater backing plate 350 provides a means to attach the resistive heater 300 to other parts in an assembly. The preferred method of attaching the heater backing plate 350 to the resistive heater 300 by a vulcanization process. The vulcanization process provides a reliable attachment method with less degradation, over time, as compared with many adhesive attachment methods. Vulcanization is a chemical curing of the rubber insulation that is attached to the heater backing plate 350 that provides an advantage of a more reliable connection between the heater backing plate 350 and the resistive heater 300. Vulcanization not only ensures a uniform and reliable connection, but helps provide a more reliable product for a entire service life which involves repeated thermal cycling. Other attachment methods that could be used to attach the heater backing plate 350 to the resistive heater 300 include, but are not limited to, adhesives, pressure sensitive adhesives (PSA), mechanical fasteners, and other similar materials. Many types of pressure sensitive adhesives (PSA) could be used to attach to attach the heater backing plate 350 to the resistive heater 300. Those skilled in the art will recognize that other methods of attaching known in the art would be within the spirit and scope of the present invention.

Prior art thermal systems do not have consistent, uniform thermal contact between the sample well caps and the heater. Inconsistent and non-uniform contact between the caps and the heater can cause inefficiencies and inaccurate results. The flexible heater cover assembly 200 of the present invention has the heater backing plate 350 helps the plate and heater assembly (FIGS. 29–32) to better contact the surface of the sample tube caps 146. The sample tube caps 146 may vary in installed height, either from tube height differences, thermal system base 15 well height differences, or cap thickness differences. The sample tube caps 146 also may be installed on the tubes in a non-uniform manner. The sample tube caps 146 may be not fully seated onto the tube, or they may be twisted such that the top horizontal surface of the sample tube cap 146 is not positioned in a horizontal plane. These differences create a design challenge for getting a consistent, uniform thermal contact between the resistive heater 300 and the sample tube caps 146. The flexibility of the heater backing plate 350 minimizes this problem by allowing flexible, consistent, uniform thermal contact for all 96 sample wells caps 146.

The preferred surface treatment of the top surface of the heater backing plate 350 is to coat the top surface of the heater backing plate 350 with a black dye through an anodization process. The black dye is added into the anodization bath because the black dye leaves the top surface of the heater backing plate 350 with a black color that is a poor optical reflector so that top surface does not reflect or scatter light from the area above one well to other adjacent wells. Any reflection or scattering of light from one well to another well contributes to optical cross-talk and decreases the quality of the optical data. The preferred black anodized top surface of the heater backing plate 350 helps to minimize optical signal background noise and scattering (signal reduction) because the black surface is less reflective in the wavelengths commonly associated with fluorescent dyes used in PCR. Many other surface treatment could be used within the spirit and scope of the present invention. Other surface treatments that could be used include, but are not limited to, natural color anodization, colored anodizations, chemical conversion film coatings and similar surface treatments. The natural color anodization leaves the top surface of the plate with its natural color, light olive to gray. The natural color anodization is simpler than cheaper than the preferred black dye anodization process because no dye is used in the natural color anodization process. In colored anodizations, the top surface of the plate takes on the color of a dye that is added during the anodization process. The chemical conversion film coating provides a mild surface protection and is widely used to treat aluminum. Those skilled in the art will recognize that other surface treatments known in the art would be within the spirit and scope of the present invention. The anodized surface also provides a more wear resistant surface to interface with a series of springs located above the heater backing plate 350. The springs contact the surface of the heater backing plate 350 and slide along the surface during loading and unloading of the sample tubes 140 as will now be discussed.

Figure 33:
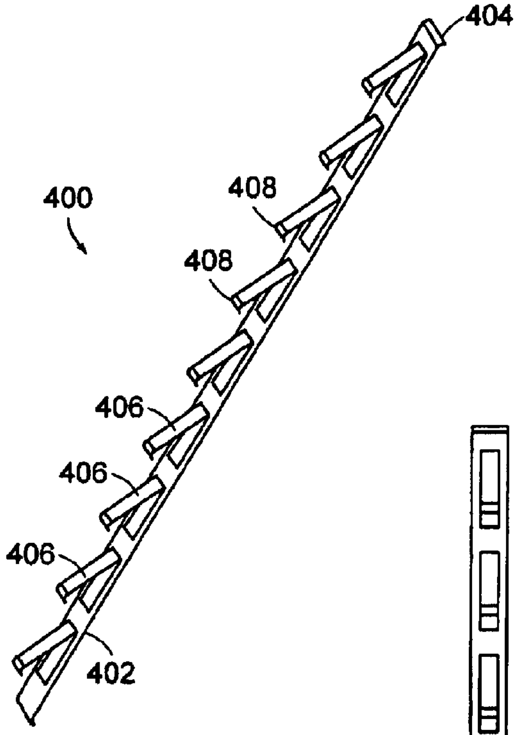
FIG. 33 is a perspective view of a spring strip of a flexible heating cover assembly of the present invention.
Figure 34:
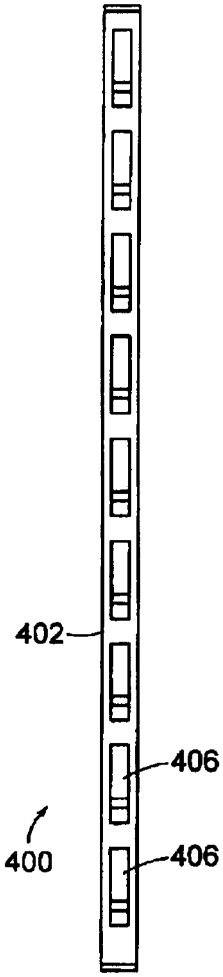
FIG. 34 is a top view of a spring strip of a flexible heating cover assembly of the present invention.
Figure 35:
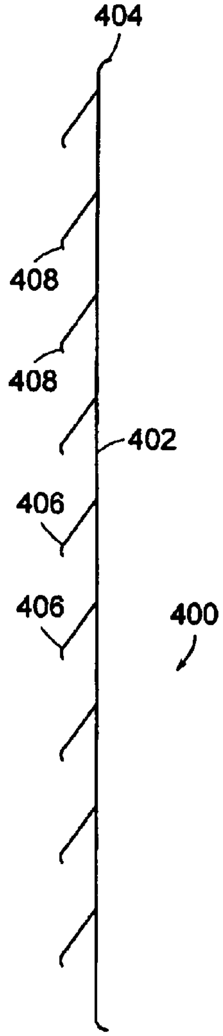
FIG. 35 is a side view of a spring strip of a flexible heating cover assembly of the present invention.

As shown in FIGS. 33–35, the flexible heating cover assembly 200 includes a plurality of spring strips 400. The spring strips 400 are located above the heater backing plate 350. In combination with the stiff support plate 500, the spring strips 400 provide a spring force to the resistive heater 300 which is distributed about the resistive heater 300 and the plurality of sample wells. The spring strips 400 includes an elongated body 402, a curved retainer lip 404, and a plurality of spring extensions 406 having an extension end 408.

In the present invention, the spring strips 400 act as cantilever springs. The spring strip 400 has a plurality of spring points. A spring point is the area of contact between the extension end 408 of the spring extension 406 and the heater backing plate 350 attached to the resistive heater 300. Each spring point corresponds to the spring extension 406 having an extension end 408. In a preferred embodiment of the present invention, the spring strip 400 has nine spring points which interface with the heater backing plate 350 attached to the resistive heater 300. The nine spring points of each spring strip 400 are spaced such that each spring point is located approximately half way between adjacent sample well centers. Thus, there is a consistent force applied to the heater backing plate 350 attached to the resistive heater 300 about each sample well. In other embodiments of the present invention, the spring strip 400 may have more or less than nine spring points (i.e., five spring points, eight spring points, ten or more spring points). Because each spring strip 400 preferably contains nine spring points (and nine spring extensions 406 that each act a spring), only a limited number of spring strips 400 need to be installed to provide a spring-like force between each of the plurality of sample wells. In a preferred embodiment of the present invention, 13 spring strips 400 are used, providing 117 spring points that can apply force to the heater backing plate 350 attached to the resistive heater 300. In other embodiments of the present invention, any number of spring strips 400 may be used to provide various force levels (i.e., five spring strips, ten spring strips, fifteen or more spring strips). The number and location of spring strips 400 used can vary to provide various force levels on the heater backing plate 350 attached to the resistive heater 300.

The spring force of the spring strips 400 is transferred from the extension end 408 of the spring extensions 406 to the heater backing plate 350 attached to the resistive heater 300. Each spring extensions 406 acts as a cantilevered spring to transfer the spring force. The spring strips 400 are configured such that the spring force is applied at the spring point between the hole centers of adjacent sample wells. For example, if there are four of the sample well holes in the central portion of the heater backing plate 350 attached to the resistive heater 300, the spring force points would be roughly located between the four sample wells. The spring force is not applied between two of the sample well holes in the heater backing plate 350 attached to the resistive heater 300 (either two columns or two rows); the spring force is applied between all four adjacent sample wells.

The preferred material of spring strips 400 is beryllium copper. Many other materials could be used within the spirit and scope of the present invention. Other materials of the spring strips 400 that could be used include, but are not limited to, stainless steel, carbon steel and similar materials. Those skilled in the art will recognize that other spring materials known in the art would be within the spirit and scope of the present invention. The preferred thickness of the spring strip 400 is 0.004 inches, although those skilled in the art will recognize that other thicknesses would be within the spirit and scope of the present invention. The preferred length of the spring strip is slightly longer than the column of sample well holes, although those skilled in the art will recognize that other lengths would be within the spirit and scope of the present invention. The spring strips 400 are cost effectively produced from a sheet of metal by laser cutting the elongated body 402, bending up or stamping the plurality of spring extensions 406, and heat treating the metal to the proper temper.

The spring strips 400 are designed to provide from about 10 grams to about 30 grams of force for each sample tube. Each spring extension 406 helps to create about 10 grams to about 30 grams of force for each sample well. Each spring extension 406 does not provide about 10 grams to about 30 grams of force itself, but helps to create about 10 grams to about 30 grams of force for each sample well. The spring strips 400 and the heater backing plate 350 attached to the resistive heater 300 combine to provide this force more uniformly for each sample tube as compared to prior art. Thus, the spring strips 400 are an improvement over installing a separate conventional spring between each of the 96 holes because the spring strips 400 use fewer parts and impart a more uniform force.

In the prior art, the heating cover was not flexible and did not promote load sharing, thus the sample tubes and sample caps that were taller would receive a higher force while the sample tubes and caps that were lower would receive a lesser force. The uneven force distribution in the prior art lead to inefficiencies and inaccurate results. While many prior art products employ a design which concentrates most of the force onto a subset of sample tubes, the design of the present invention provides superior load sharing among sample tubes through the enhanced flexibility of the heater assembly.

The flexible heating cover assembly 200 of the present invention provides more uniform load sharing among the sample tubes through enhanced flexibility. Because the heater backing plate 350 attached to the resistive heater 300 has a stiffness and because of the location and force of the spring strips 400, the flexible heater cover assembly 200 of the present invention provides a flexible heater that promotes better and more uniform contact with each sample cap, even if the sample caps are distorted, twisted, at slightly different elevations, or at different angles relative to the horizontal plane. Because all sample tubes and sample caps will be at slightly different heights, the load on each sample tube will be non-uniform and different. Due to the flexibility and resulting distribution of force of the present invention, there is less of a force increase on the taller sample tubes and caps, and a smaller force differential on shorter sample tubes and caps. An advantage of the load sharing design of the present invention is a reduced risk of sample tube or sample cap damage (and biological material contamination) from too much force imparted onto a few sample tubes or sample caps. Another advantage of the load sharing design of the present invention is a more uniform force in a vertical direction for each sample tube so that a more uniform thermal resistance path is created between the conical wall of the sample tube and the sample well wall of the thermal system base 15 which results in better thermal uniformity among biological samples. Another advantage of the load sharing design of the present invention is that flat or domed sample caps may be used to provide flexibility in optimizing the optical properties of the radiation path. Another advantage of the load sharing design of the present invention is that robotic loading and unloading of sample tubes is promoted due to the lower overall force and due to the elimination of damaged tube caps. The load sharing of the present invention helps to yield more accurate results and increase efficiency. Those skilled in art will recognize these advantages and other advantages of the flexible load sharing design of the present invention.

Although the spring strips 400 act as cantilever springs, many other spring designs could be used within the spirit and scope of the present invention. Other spring designs that could be used include, but are not limited to, a compression spring, a circular spring, a wave washer-type spring, a conical spring, a Belleville spring/washer and similar springs. Compression springs are open-coiled helical springs that offer resistance to compressive forces applied axially. Such springs are usually coiled as a constant diameter cylinder; other common forms are conical, tapered, concave, convex, and combinations of these. Most compression springs are manufactured in round wire because this offers the best performance and is readily available and suited to standard coiler tooling—but square, rectangular, or special-section wire can be specified. A wave washer-type spring is basically a circular spring that has a different inside coil diameter and an outside coil diameter and the spring may be wavy as you work your way around the perimeter to create a spring. The inside coil diameter of a spring is the diameter of the cylindrical envelope formed by the inside surface of the coils of a spring. The outside coil diameter of a spring is the diameter of the cylindrical envelope formed by the outside surface of the coils of a spring. A Belleville spring, disc spring, conical compression washer are all names for the same type of spring. A Belleville spring, also called Belleville washer, is a conical disk spring. The load is applied on the periphery of the circle and supported at the bottom. Belleville springs are used in a variety of applications where high spring loads are required. Belleville springs are particularly useful where vibration, differential thermal expansion, relaxation, and bolt creep are problems. A Belleville spring washer is a washer in the form of a cone, of constant material thickness, used as a compression spring. Unlike compression springs, Belleville spring washers can accommodate exceptionally high loads in restricted spaces. Those skilled in the art will recognize that other springs known in the art would be within the spirit and scope of the present invention.

Figure 36:
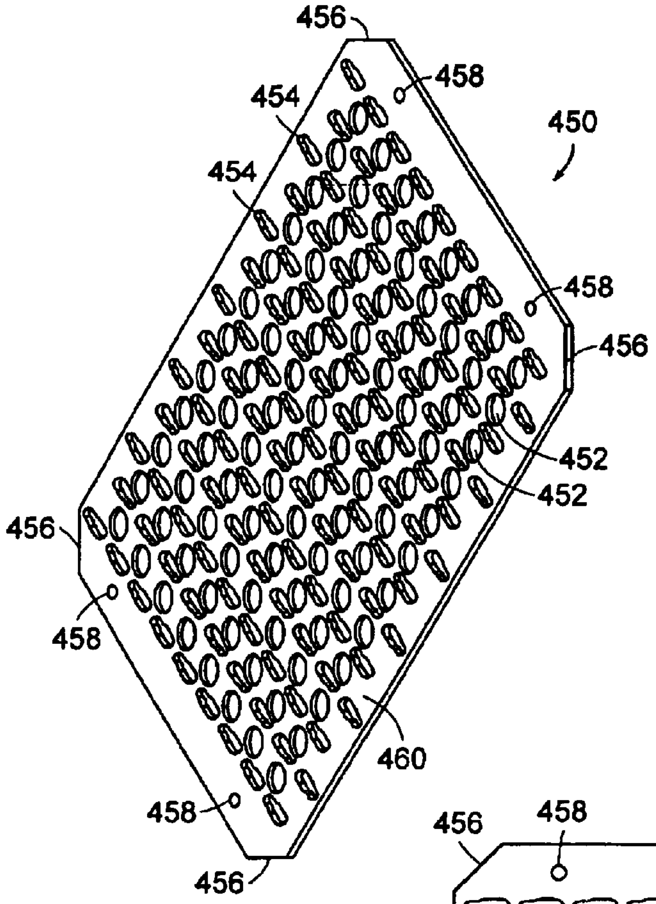
FIG. 36 is a perspective view of a spring retainer plate of a flexible heating cover assembly of the present invention.
Figure 37:
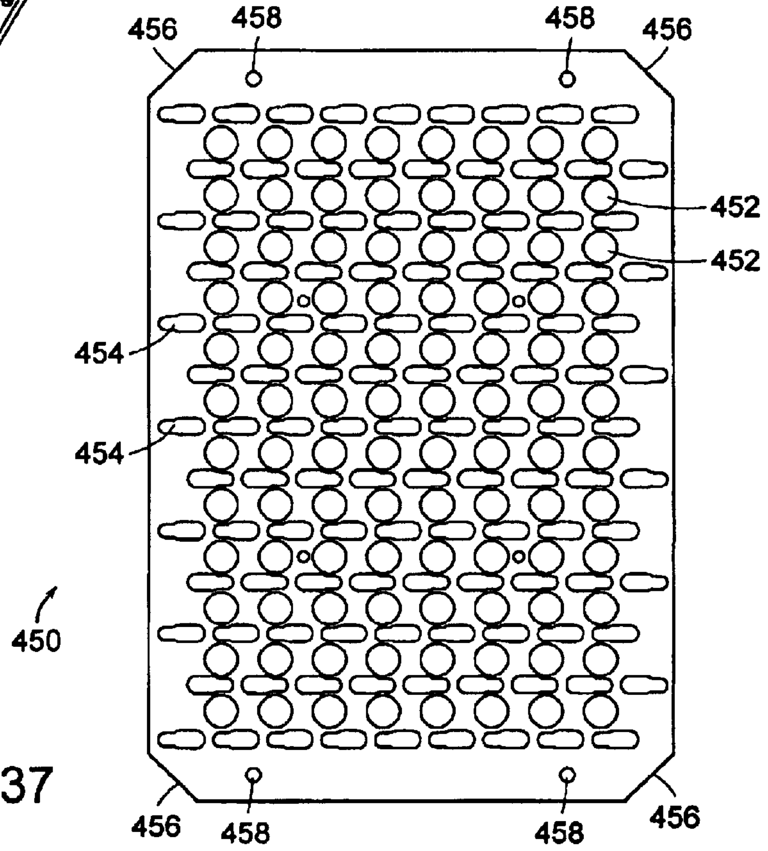
FIG. 37 is a top view of a spring retainer plate of a flexible heating cover assembly of the present invention.

As shown in FIGS. 36 and 37, the spring retainer plate 450 includes a plurality of sample well holes 452, a plurality of slots 454, a plurality of notched corner 456, a plurality of securing holes 458, and a top surface 460. The spring retainer plate 450 is used to retain the plurality of spring strips 400. The spring retainer plate 450 contains the plurality of slots 454 that allows the plurality of spring extensions 406 of each spring strip 400 to pass through the spring retainer plate 450. In assembly of the flexible heating cover of the present invention, the spring strip 400 is placed above the top surface 460 of the spring retainer plate 450 and the spring strip 400 is lowered so that the spring extensions 406 of each spring strip 400 pass through the plurality of slots 454 of the spring retainer plate 450. The spring strip 400 is lowered until the elongated body 402 of each spring strip 400 engages the top surface 460 of the spring retainer plate 450. The spring retainer plate 450 retains the spring strips 400 in the vertical direction and also provides a mechanical stop to prevent over travel for each spring strip 400. Such over travel could yield the spring material and degrade the force applied to the heater backing plate 350 attached to the resistive heater 300. The spring retainer plate 450 also contains the a plurality of notched corner 456 which allow for easier manipulation of the spring retainer plate 450 during assembly of the spring retainer plate 450.

In a preferred embodiment of the present invention, the spring retainer plate 450 is are composed of aluminum alloy 1100 with a temper designation of H12 or H14. Other aluminum alloys that could be used within the spirit and scope of the present invention include, but are not limited to, aluminum 6061, aluminum 6063, and similar aluminum alloys. Aluminum alloy 6061 is a common form of aluminum and has a wide rang of uses. Aluminum alloy 6063 is an architectural grade of aluminum that is widely used in industry. Those skilled in the art will recognize that other aluminum alloys known in the art would be within the spirit and scope of the present invention. In addition, other similar materials that could be used include, but are not limited to, polycarbonate (PC) (common trade names include lexan), polyetherimide (PEI) (common trade names include ultem), and similar materials. Those skilled in the art will recognize that other materials and alloys known in the art would be within the spirit and scope of the present invention.

The plurality of securing holes 458 of the spring retainer plate 450 allow for mechanical attachment of the spring retainer plate 450 to the stiff support plate 500 with common fasteners placed through the plurality of securing holes 458. The preferred method of attaching the spring retainer plate 450 to the stiff support plate 500 is by screwing using common small screws. Other attachment methods that could be used for the attaching the spring retainer plate 450 to the stiff support plate 500 include, but are not limited to, adhesives, glues, rivets, blind fasteners, mechanical snapping and other mechanical fasteners. Those skilled in the art will recognize that other methods of attaching the spring retainer plate 450 to the stiff support plate 500 known in the art would be within the spirit and scope of the present invention.

Figure 38:
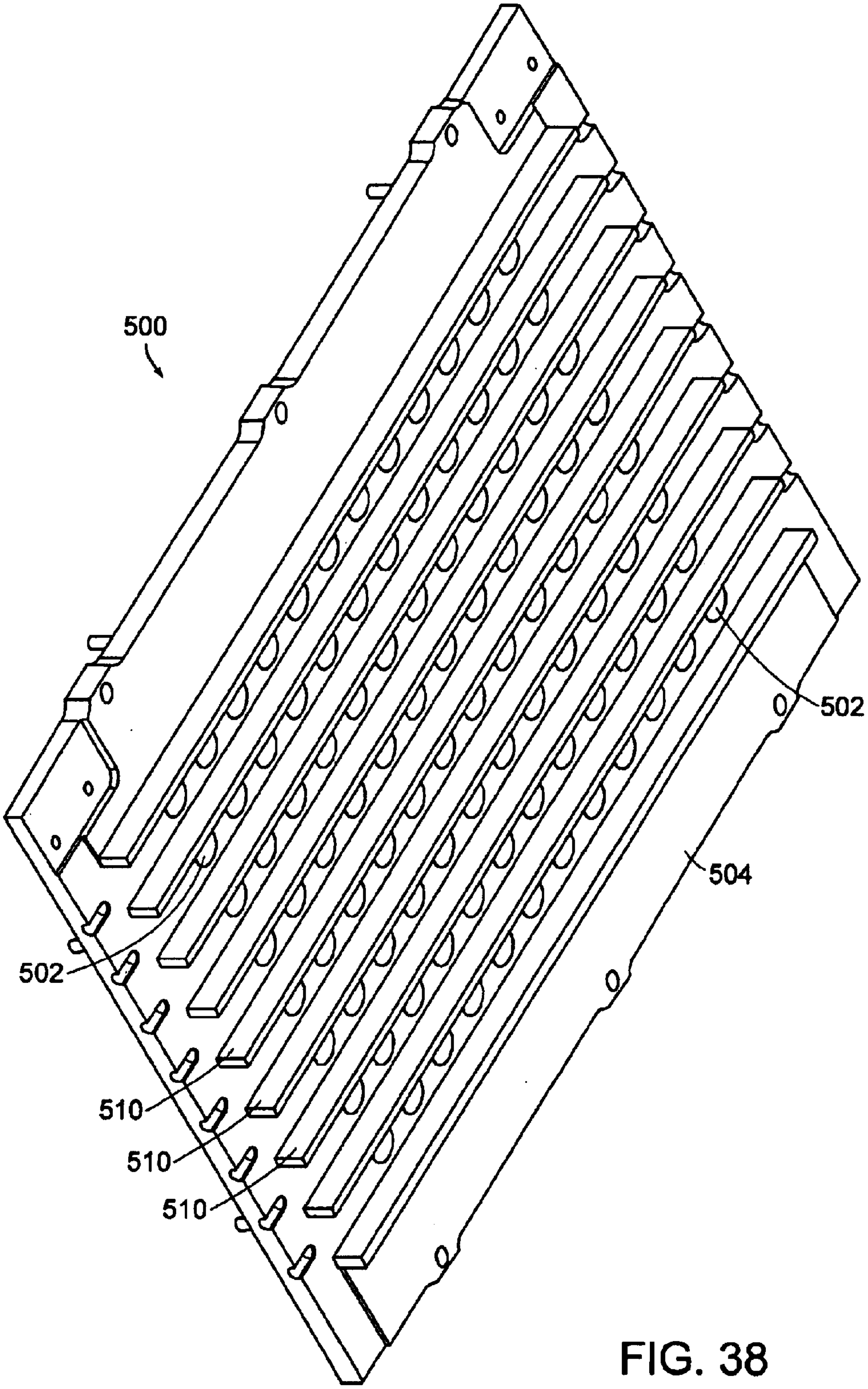
FIG. 38 is a top perspective view of a stiff support plate of a flexible heating cover assembly of the present invention.
Figure 39:
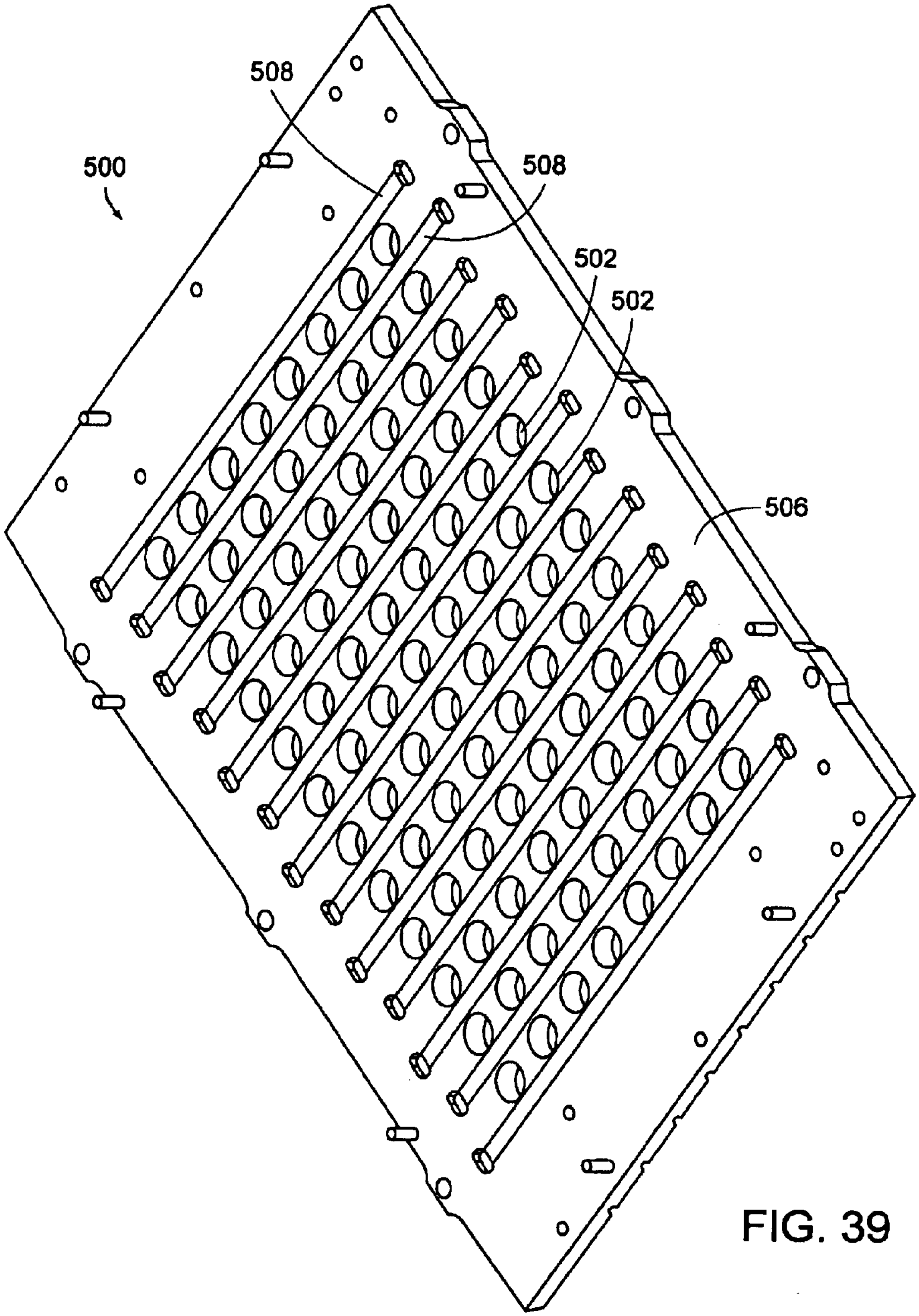
FIG. 39 is a bottom perspective view of a stiff support plate of a flexible heating cover assembly of the present invention.

As shown in FIGS. 38 and 39, the stiff support plate 500 includes a plurality of sample well holes 502, a top surface 504, a bottom surface 506, a plurality of spring slots 508, and a plurality of ribs 510. The stiff support plate 500 is used to provide stiffness for the spring strips 400. The plurality of sample well holes 502 in the stiff support plate 500 permit emitted radiation to pass through the holes 502 to reach optical scanning equipment that collects optical data collected for quantitative PCR type experiments.

As best shown in FIG. 39, the plurality of spring slots 508 are located on the bottom surface 506 of the stiff support plate 500. The spring slots 508 act to locate the spring strips 400 in the horizontal plane and the bottom of the spring slots 508 act to locate the spring strips 400 in at least partially in the vertical direction. Preferably, the stiff support plate 500 contains the spring slots 508 for 13 spring strips 400, those skilled in the art will recognize the any number of the spring slots 508 could be machined in the bottom surface 506 of the stiff support plate 500 for use with alternate configurations of spring strips 400 discussed above.

The performance objectives of the stiff support plate 500 include, but are not limited to, the following: (1) a stiffness measure—a force versus deflection profile across the stiff support plate 500; (2) a stiff support plate 500 thickness that would effect the stiffness and also affect the optical sensitivity. The stiffness of the stiff support plate 500 is sufficient to provide a reaction force for all spring strips with minimal deflection of the stiff support plate 500. In this manner, the stiff support plate 500 retains its nearly planar shape under loading force from the spring strips 400, while the loading force from the bottom side of the spring strips 400 act to deform the heater backing plate 350 attached to the resistive heater 300.

As best shown in FIG. 38, the plurality of ribs 510 are located on the top surface 506 of the stiff support plate 500. The plurality of ribs 510 provide stiffness to the stiff support plate 500 while permitting the close travel of optical scanning equipment to pass between the ribs 510. The optical scanning equipment can move in a near constant velocity scanning motion or a point-to-point, move and hover type scanning motion to promote the emission and collection of radiation into and out of the flexible heating cover assembly 200 and the sample tubes 140. The close travel of the optical scanning equipment to the stiff support plate 500 promotes the sensitivity of the optical data collected for quantitative PCR type experiments. The rib 510 orientation, quantity, thickness and height all would play into stiffness and would also be specific to the method of optical data collection (i.e., scanning or some other type of optical data collection). In an alternative embodiments of the present invention where an optical detector is placed above each of the sample wells 24 (instead of optically scanning) then the ribs 510 would not be necessary and a cavity or a counter bore around each of the sample wells 24 would suffice. In other alternative embodiments of the present invention using different scanning approaches, many combinations of the physical parameters of the stiff support plate 500 could be varied to achieve its performance. For example, with a smaller force range (about 10 to about 16 grams per well), the stiff support plate 500 could be optimized by decreasing the stiffness of the stiff support plate 500 and gaining some optical sensitivity. Thus, the optical sensitivity could be enhanced at the expense of some of the stiffness with a smaller force range.

Preferably, the stiff support plate 500 is composed of aluminum alloy 6061-T6. Many other materials with sufficient stiffness could be used within the spirit and scope of the present invention. Other materials that could be used to fabricate the stiff support plate 500 include, but are not limited to, other aluminum alloys (1100, 6063, 5032), polyetherimide (PEI) (common trade names include ultem), titanium, titanium alloys, stainless steel, carbon steel, beryllium-aluminum alloys, and similar materials.

Beryllium-aluminum alloys are fairly rare and can be easily cast and retain exceptional stiffness versus weight properties. Beryllium-aluminum alloys may be used as a cast part for the stiff support plate to keep the fabrication cost low, while providing an optical sensitivity advantage by making the stiff support plate thinner, or reducing the rib height, or deleting the ribs. Stainless steel or carbon steel have a modulus of the material that would yield a stiffer stiff support plate 500. Titanium has about 50% better stiffness than aluminum, but has about 50% more weight than aluminum. Those skilled in the art will recognize that other materials known in the art would be within the spirit and scope of the present invention. The stiff support plate 500 is preferably 0.130 inches thick through a section between the ribs 510. The ribs 510 preferably extend 0.165 inches above the top of the stiff support plate 500. The preferred rib thickness is 0.048 inches. Those skilled in the art will recognize that other combinations of rib height, rib thickness, rib quantity, rib orientation, and plate thickness, size, and material, are within the spirit and scope of the invention.

The stiff support plate 500 is also coated with a black dye through an anodization process to minimize optical signal background noise and scattering (signal reduction). The black dye is added into the anodization bath because the black dye leaves the stiff support plate 500 with a black color that is a poor optical reflector so that top surface does not reflect or scatter light from the area above one well to other adjacent wells. Any reflection or scattering of light from one well to another well contributes to optical cross-talk and decreases the quality of the optical data. The preferred black anodized top surface of the stiff support plate 500 helps to minimize optical signal background noise and scattering (signal reduction) because the black surface is less reflective in the wavelengths commonly associated with fluorescent dyes used in PCR. Many other surface treatment could be used within the spirit and scope of the present invention. Other surface treatments that could be used include, but are not limited to, natural color anodization, colored anodizations, chemical conversion film coatings and similar surface treatments. The natural color anodization leaves the top surface of the plate with its natural color, light olive to gray. The natural color anodization is simpler than cheaper than the preferred black dye anodization process because no dye is used in the natural color anodization process. In colored anodizations, the top surface of the plate takes on the color of a dye that is added during the anodization process. The chemical conversion film coating provides a mild surface protection and is widely used to treat aluminum. Those skilled in the art will recognize that other surface treatments known in the art would be within the spirit and scope of the present invention.

The stiff support plate 500 also contains other mechanical features which can be used to attach various skirt components 250 to achieve an ambient environment around the upper portion of the sample tubes 140 and sample tubes caps 146 which is favorable. The stiff support plate 500 and various skirt components 250 minimize the convective heat loss and minimize any convective air flow disruptions which could degrade the target temperature of the flexible heater assembly 200 or the thermal system base 15.

Figure 40:
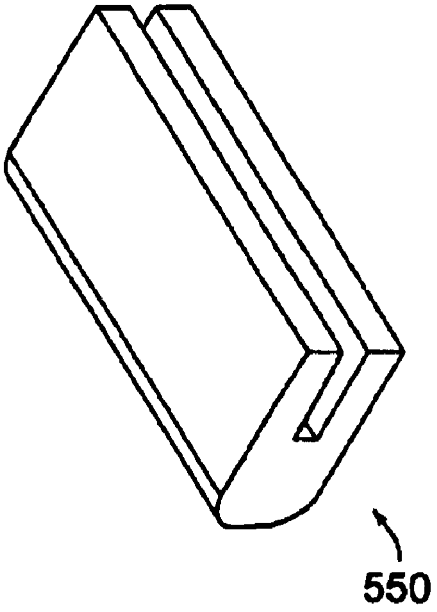
FIG. 40 is a perspective view of a heater slide of a flexible heating cover assembly of the present invention.
Figure 41:
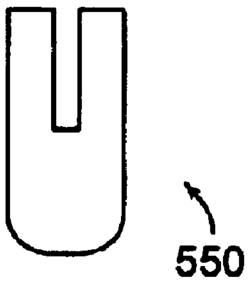
FIG. 41 is a front view of a heater slide of a flexible heating cover assembly of the present invention showing the U-shape of the preferred heater slide.

As shown in FIGS. 40 and 41, the flexible heater cover assembly 200 of the present invention includes a plurality of heater slides 550. The heater slide 550 is used to locate and guide the heater backing plate 350 attached to the resistive heater 300 within the cover assembly. The heater slide 550 controls the heater backing plate 350 attached to the resistive heater 300 position in the horizontal plane, while permitting some freedom of movement in the vertical direction with a minimum reaction force from friction imparted to the heater backing plate 350 attached to the resistive heater 300. The heater slide 550 interfaces with a slot along the outer edges of the heater backing plate 350 attached to the resistive heater 300.

The flexible heater cover assembly 200 of the present invention includes a plurality of heater slides 550. In a preferred embodiment of the present invention, four heater slides 550 are used. The four heater slides 550 are located about the heater backing plate 350 attached to the resistive heater 300 in a symmetrical manner relative to the plurality of sample well holes 312, 352. In this way, the thermal effect from the contact of the heater slides 550 is symmetrical so that any impact to the temperature gradient about the heater backing plate 350 attached to the resistive heater 300 is symmetrical to the plurality of sample well holes 312, 352. In other embodiments of the present invention, any number of heater slides 550 could be used (i.e., one heater slide, two heater slides, three heater slides, or five or more heater slides). In embodiments of the present invention using more or less than fours heater slides 550, the size, shape, orientation and configuration of the heater slides may be modified. For example, in an embodiment of the present invention that uses two heater slides, the heater slides my be very long. Those skilled in the art will recognize that other sizes, shapes, quantities, orientations and configurations of the heater slides 550 could be used within the spirit and scope of the invention.

The heater slide 550 should be shaped to have a minimal contact with the heater backing plate 350 attached to the resistive heater 300 so the desired non-uniform heat distribution is maintained. In a preferred embodiment of the present invention, the heater slide 550 is U-shaped. Many other shapes of the heater slides 550 could be used within the spirit and scope of the present invention. Other shapes of the heater slides 550 include, but are not limited to, a rectangular block, a cylinder, a stretched shape that is long and thin, and other similar shapes. Those skilled in the art will recognize that other shapes known in the art would be within the spirit and scope of the present invention.

Preferably, the heater slide 550 is composed of acetal, a plastic material. Acetals, technically polyoxymethylenes (POM), are highly crystalline engineering thermoplastic resins. Acetal is commercially available under the common trade name include delrin. Acetal performance characteristics combine high strength and rigidity, unusual resilience, outstanding static and dynamic fatigue resistance, natural lubricity, and resistance to a wide range of solvents, oils, greases and chemicals. Very low moisture absorption results in excellent dimensional stability, and maintenance of performance characteristics over a wide range of humidity. Many other materials with similar low friction properties while subjected to a PCR temperature environment around 100° C. for extended time periods could be used within the spirit and scope of the present invention. Other materials having similar characteristics of excellent mechanical, thermal and chemical properties, wide range of temperature for an extended period, good self-lubrication, friction-resistance and abrasion-resistance, high rigidity and conductivity could be used to fabricate the stiff plate include, but are not limited to, Acrylonitrile-Butadiene-Styrene (ABS), other styrene-based materials, polyvinylchloride (PVC), polyamide (common trade names include zytel and nylon), polypropylene, vinyl, polycarbonate, polytetrafluoroethylene (PTFE) (common trade names include teflon), pet, pbt, tpr, tpe, acrylic, polystyrene, other plastics, titanium, titanium alloys, stainless steel, carbon steel and similar materials. Styrene-based materials offer unique characteristics of durability, high performance, versatility of design, simplicity of production, and economy and provide excellent hygiene, sanitation, and safety benefits. Those skilled in. the art will recognize that other materials known in the art would be within the spirit and scope of the present invention.

The means for attaching the various components of the flexible heater cover assembly 200 will now be described. It is important that the means for attaching the various components does not result in significant heat transfer away. The attachment fasteners attach the cover assembly skirt 250, the resistive heater 300, the heater backing plate 350, the spring strip 400, the spring retainer plate 450, the stiff support plate 500, and the plurality of heater slides 550. The aforementioned components engage each other to form the flexible heating cover assembly 200. The attachment fasteners have been designed to minimize the heat transfer that occurs through the attachment fasteners. It should be understood that any attachment fasteners known in the art may be used including, but not limited to, screws, nuts and bolts, rivets, welds, adhesives, and other mechanical connectors.

The flexible heating cover assembly 200 requires a means which acts as a clamping function between the flexible heating cover assembly 200 and the thermal system base 15. The clamping function should provide at least three important characteristics. First, the clamping function should sufficiently generate a clamping force which is greater in magnitude than the total force created by the spring force system in the flexible heating cover assembly which imparts force into the sample tubes 140 and sample tube caps 146 and into the thermal system base 15. Second, the clamping function should generate the force in a direction which is nearly vertical, or the vertical component of a force which is not vertical must have a magnitude which satisfies the first clamping function characteristic. Also, the nearly vertical force or component of a non-vertical force must be directed downward, assuming that the position of the thermal system base 15 is below the flexible heating cover assembly 200. Third, the clamping function should apply the force in a plurality of locations. In a preferred embodiment of the present invention, the force is applied at four locations. The four force locations are approximately about each corner of the flexible heating cover assembly 200: front left corner, front right corner, rear left corner, and rear right corner. In an alternative embodiment of the present invention, two force locations may be employed. For example, a manually operated instrument sample loading scheme could have two force locations. In the alternative embodiment having two force locations, a first force location would preferably be located along the left side of the flexible heating cover assembly 200, about midway front to back. A second force location would preferably be located along the right side of the flexible heating cover assembly 200, about mid way front to back. For the two force location embodiment, the interfacing locations on the flexible heating cover assembly 200 structure would be revised such that their numbers and locations would be consistent with the two force location embodiment. The details of a mechanism or a manual clamp to accomplish the clamping function are known to those skilled in the art. Mechanisms for accomplishing the clamping function include, but are limited to, a manual lever or clamp, an automated lever or clamp, a latch mechanism, a spring over center design, Those skilled in the art will recognize that a variety of clamping function designs could be employed to satisfy the needs of the flexible heating cover assembly 200 are be within the spirit and scope of the present invention.

The operation of the flexible heating cover assembly 200 attached to the thermal system base 15 will be described below. The flexible heating cover assembly 200 of the present invention is opened up by pivoting about hinges. A tray of disposable sample tubes. 140 are placed so that the sample tubes 140 are positioned in the sample wells 24. The flexible heating cover assembly 200 is then closed.

Thermal cycling can now be performed. The thermal cycling is controlled by a controller. During thermal cycling, the DNA will undergo a pre-programmed thermal cycling process of raising and lowering temperatures in order to replicate the strands of DNA. Before undergoing the process, the temperature of the thermal block assembly 20 is measured at at least one location. The controller then calculates the desired temperature of the thermal block assembly 20 at the particular time. The desired temperature is then compared to the measured temperature. If the measured temperature is less than the desired temperature, heating of the thermal block assembly 20 will occur. Heating the thermal block assembly 20 comprises several steps. The first step is imparting a first heat rate via at least one first heater, a portion of the first heat rate being transferred to the thermal block assembly 20. The second step is imparting a second heat rate via a second heater, a portion of the second heat rate being transferred to the first heater. The third step is imparting a third heat rate via a third heater, a portion of the third heat rate being transferred to the top of the sample tubes in order to reduce the likelihood of condensation occurring on the top of sample tubes. It is understood that all three of these steps may be performed simultaneously.

Because a plurality of first heaters may be provided, the heat rate output of each of the plurality of first heaters may be independently controlled. This will allow the controller to monitor the sensor cup temperatures so that all of the sensor cups have a substantially equal temperature. Likewise, if a plurality of second heaters is provided, the heat rate output of each of the second heaters may also be independently controlled.

However, if the measured temperature is greater than the desired temperature, heating does not occur but instead the thermal block assembly will be cooled. This is done by reversing the current on the Peltier heaters 40 in order to turn them into coolers, and by also imparting a cooling convection current on the heat sink which is thermally coupled to the thermal block assembly to provide heat transfer from the thermal block assembly to ambient air adjacent the heat sink. A radial fan may be provided for providing the convection current to the heat sink.

Once the step of heating or cooling is performed, the cycle continues by repeating the steps of measuring, calculating, and comparing until the predetermined thermal cycle for the samples of biological reaction mixture is completed. After the proper number of cycles have been performed, the flexible heating cover assembly 200 will be opened and the DNA sample tubes will be removed from the sample wells.

The thermal system base 15 could also be modified to incorporate a temperature gradient means across the thermal block assembly 20. A thermal system base 15 with a temperature gradient means is used to discover the optimum polymerase chain reaction annealing stage temperatures. The thermal system base 15 is primarily focused towards producing the DNA via polymerase chain reactions once these temperatures are known. However, the thermal system base 15 could be modified to include a temperature gradient means or independent temperature zones.

The flexible heating cover assembly 200 of the present invention provides superior multiplexing performance, increases throughput, decreases reagent costs, allows more stringent control protocols, expands data analysis and display options, provides ease of use and flexibility, safeguards the data, increases reliability, and decreases maintenance and service. The flexible heating cover assembly 200 of the present invention is also compatible with numerous fluorescent chemistries (i.e., primers, probes, dyes, and the like).

The flexible heating cover assembly 200 when used in conjunction with the thermal system base 15 is advantageous over the prior art for its precision, speed, and uniformity. The flexible heating cover assembly 200 is precise because the cycling temperatures of the sample block are regulated by a hybrid system of Peltier, resistive, and convective technologies for tight temperature control. The flexible heating cover assembly 200 is fast because design features of the sample block increase the thermal ramping rate. For example, a forty-cycle QPCR protocol can be completed in less than one and one-half hours. The flexible heating cover assembly 200 provides uniformity because the thermal cycler has unparalleled thermal accuracy—about ±0.25° C. variation in sample temperature across the 96-well plate for optimal cycling conditions.

The flexible heating cover assembly 200 when used in conjunction with the thermal system base 15 requires no additional pipetting or handling of samples because amplification and detection occur in the same sample tube. The thermal plate holds reactions in a standard 96-well format, for high throughput of samples. Reactions are cycled within well-controlled temperature specifications that avoid reduction of enzyme half-life and non-specific PCR product formation. Ideal temperature conductivity is achieved through the cone-shaped geometric design of the sample wells. The design not only maximizes contact between the sample wells and thermal block it also minimizes mass for high-speed thermal ramping.

It will be apparent to those skilled in the art that various modifications and variations can be made in the design and construction of the flexible heater cover assembly of the present invention without departing from the scope or spirit of the invention.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A flexible heating cover assembly comprising:

a housing including a plurality of engageable enclosure components;

a resistive heater located within the housing, the resistive heater including a plurality of heater element areas;

a heater backing plate engaging the resistive heater and providing stability to the resistive heater;

a force distribution system that engages the heater backing plate and distributes a force over the heater backing plate; and a support plate providing stiffness for the force distribution system, wherein the arrangement of the resistive heater, the heater backing plate, the force distribution system and the support plate provide substantial temperature uniformity among a plurality of sample tubes for receiving samples of biological material.

2. The flexible heating cover assembly of claim 1 wherein the housing further comprises a pair of end caps and a pair of side bars all composed of a thermally insulating material.

3. The flexible heating cover assembly of claim 1 wherein the resistive heater is thin to allow rapid heating and cooling during thermal cycling of the plurality of sample tubes.

4. The flexible heating cover assembly of claim 1 wherein the resistive heater produces a non-uniform heat distribution along a surface exposed to the plurality of sample tubes.

5. The flexible heating cover assembly of claim 1 wherein the resistive heater further comprises a plurality of heater element areas including at least one outer heater element area and at least one central heater element area.

6. The flexible heating cover assembly of claim 5 wherein the at least one outer heater element area is C-shaped and located along an outer edge of a plurality of sample well openings.

7. The flexible heating cover assembly of claim 5 wherein the at least one outer heater element area includes a tapered portion and curved end portions.

8. The flexible heating cover assembly of claim 1 wherein the resistive heater further comprises at least one heat carrier circuit that is not electrically connected to a heater power source wherein the at least one heat carrier circuit transfers heat through the resistive heater.

9. The flexible heating cover assembly of claim 1 wherein the resistive heater further comprises a thermistor located toward a center portion of the resistive heater to provide control of the vapor and the condensation environment of the plurality of sample tubes.

10. The flexible heating cover assembly of claim 1 wherein the resistive heater can move vertically within the flexible heating cover assembly to provide a more uniform heat distribution.

11. The flexible heating cover assembly of claim 1 wherein the heater backing plate is thin to promote flexibility when the heater backing plate is connected to the resistive heater.

12. The flexible heating cover assembly of claim 1 wherein the heater backing plate is composed of a thermally conductive material.

13. The flexible heating cover assembly of claim 1 wherein the heater backing plate further comprises a plurality of narrow slots to promote the flexibility of the heater backing plate and minimize the retardation of heat transfer through the heater backing plate.

14. The flexible heating cover assembly of claim 1 wherein a top surface of the heater backing plate is treated to minimize reflecting or scattering of light from the top surface of the heater backing plate.

15. The flexible heating cover assembly of claim 1 wherein the force distribution system further comprises at least one spring strip and a spring retainer plate.

16. The flexible heating cover assembly of claim 15 wherein the at least one spring strip has an elongated body and a plurality of spring extensions.

17. The flexible heating cover assembly of claim 16 wherein the plurality of spring extensions distribute the force uniformly on the heater backing plate.

18. The flexible heating cover assembly of claim 16 wherein the spring retainer plate retains the at least one spring strip and allows the plurality of spring extensions of the at least one spring strip to pass through the spring retainer plate.

19. The flexible heating cover assembly of claim 1 wherein the support plate has sufficient stiffness to provide a reaction force for the force distribution system with minimal deflection of the support plate.

20. The flexible heating cover assembly of claim 1 wherein the support plate retains a substantially planar shape under a loading force from the force distribution system, while the loading force acts to deform the heater backing plate attached to the resistive heater.

21. The flexible heating cover assembly of claim 1 wherein the support plate has a plurality of ribs located on a top surface of the support plate to provide stiffness to the support plate while permitting the close travel of optical scanning equipment to pass between the plurality of ribs.

22. The flexible heating cover assembly of claim 1 further comprising at least one heater slide to locate and guide the heater backing plate attached to the resistive heater in the flexible heating cover assembly.

23. The flexible heating cover assembly of claim 1 wherein at least one heater slide controls a horizontal position of the heater backing plate attached to the resistive heater, while permitting some freedom of movement in a vertical direction.

24. The flexible heating cover assembly of claim 1 wherein the resistive heater, the heater backing plate, and the support plate each comprise a plurality of aligned sample well openings, each sample well opening corresponding to a respective sample tube of the plurality of sample tubes.

25. The flexible heating cover assembly of claim 1 further comprising an optical scanning equipment that collects optical data for quantitative PCR type experiments.

26. The flexible heating cover assembly of claim 1 wherein a plurality of mechanical interfaces transfer force between the flexible heating cover assembly and a thermal system base.

27. The flexible heating cover assembly of claim 1 wherein the flexible heating cover assembly surrounds the top and extends over at least a portion of a side of a thermal system base.

28. The flexible heating cover assembly of claim 1 wherein the flexible heating cover assembly holds the plurality of sample tubes in a plurality of sample wells of a thermal system base by imparting a substantially uniform compressive force on the plurality of sample tubes.

29. The flexible heating cover assembly of claim 1 wherein the flexible heating cover assembly tends to thermally insulate the plurality of sample tubes.

30. The flexible heating cover assembly of claim 1 wherein each sample tube extends for a substantial length in the flexible heating cover assembly.

31. The flexible heating cover assembly of claim 1 wherein the flexible heating cover assembly is capable of withstanding thermally cycling of the samples of biological material.

32. The flexible heating cover assembly of claim 1 wherein the flexible heating cover assembly helps to minimize the convective heat loss to an ambient environment.

33. A cover assembly for an apparatus for heating samples of biological material, comprising:

a housing including a plurality of engageable enclosure components;

a resistive heater located within the housing, the resistive heater including at least one outer heater element area and at least one central heater element area;

a heater backing plate engaging the resistive heater to provide protection and stability to the resistive heater, wherein the heater backing plate is thin and composed of a thermally conductive material;

a force distribution system comprising at least one spring strip and a spring retainer plate, the force distribution system engaging the heater backing plate to distribute a force over the heater backing plate; and a support plate providing sufficient stiffness to provide a reaction force for the force distribution system with minimal deflection of the support plate, wherein the arrangement of the resistive heater, the heater backing plate, the force distribution system and the support plate provide substantial temperature uniformity among a plurality of sample tubes for receiving samples of biological material.

34. The cover assembly of claim 33 wherein the housing further comprises a pair of end caps and a pair of side bars all composed of a thermally insulating material.

35. The cover assembly of claim 33 wherein the resistive heater is thin to allow rapid heating and cooling during thermal cycling of the plurality of sample tubes.

36. The cover assembly of claim 33 wherein the resistive heater produces a non-uniform heat distribution along a surface exposed to the plurality of sample tubes.

37. The cover assembly of claim 33 wherein the at least one outer heater element area is C-shaped and located along an outer edge of a plurality of sample well openings.

38. The cover assembly of claim 33 wherein the at least one outer heater element area includes a tapered portion and curved end portions.

39. The cover assembly of claim 33 wherein the resistive heater further comprises at least one heat carrier circuit that is not electrically connected to a heater power source wherein the at least one heat carrier circuit transfers heat through the resistive heater.

40. The cover assembly of claim 33 wherein the resistive heater further comprises a thermistor located toward a center portion of the resistive heater to provide control of the vapor and the condensation environment of the plurality of sample tubes.

41. The cover assembly of claim 33 wherein the resistive heater can move vertically within the flexible heating cover assembly to provide a more uniform heat distribution.

42. The cover assembly of claim 33 wherein the heater backing plate further comprises a plurality of narrow slots to promote the flexibility of the heater backing plate and minimize the retardation of heat transfer through the heater backing plate.

43. The cover assembly of claim 33 wherein a bottom surface of heater backing plate is connected to the resistive heater to provide protection and stability to the resistive heater.

44. The cover assembly of claim 33 wherein a top surface of the heater backing plate is treated to minimize reflecting or scattering of light from the top surface of the heater backing plate.

45. The cover assembly of claim 33 wherein the at least one spring strip has an elongated body and a plurality of spring extensions.

46. The cover assembly of claim 45 wherein the plurality of spring extensions distribute the force uniformly on the heater backing plate.

47. The cover assembly of claim 45 wherein the spring retainer plate retains the at least one spring strip and allows the plurality of spring extensions of the at least one spring strip to pass through the spring retainer plate.

48. The cover assembly of claim 33 wherein the support plate retains a substantially planar shape under a loading force from the force distribution system, while the loading force acts to deform the heater backing plate attached to the resistive heater.

49. The cover assembly of claim 33 wherein the support plate has a plurality of ribs located on a top surface of the support plate to provide stiffness to the support plate while permitting the close travel of optical scanning equipment to pass between the plurality of ribs.

50. The cover assembly of claim 33 further comprising at least one heater slide to locate and guide the heater backing plate attached to the resistive heater in the flexible heating cover assembly.

51. The cover assembly of claim 33 wherein at least one heater slide controls a horizontal position of the heater backing plate attached to the resistive heater, while permitting some freedom of movement in a vertical direction.

52. The cover assembly of claim 33 wherein the resistive heater, the heater backing plate, and the support plate each comprise a plurality of aligned sample well openings, each sample well opening corresponding to a respective sample tube of the plurality of sample tubes.

53. The cover assembly of claim 33 further comprising an optical scanning equipment that collects optical data for quantitative PCR type experiments.

54. The cover assembly of claim 33 wherein a plurality of mechanical interfaces transfer force between the flexible heating cover assembly and a thermal system base.

55. The cover assembly of claim 33 wherein the flexible heating cover assembly surrounds the top and extends over at least a portion of a side of a thermal system base.

56. The cover assembly of claim 33 wherein the flexible heating cover assembly holds the plurality of sample tubes in a plurality of sample wells of a thermal base system by imparting a substantially uniform compressive force on the plurality of sample tubes.

57. The cover assembly of claim 33 wherein the flexible heating cover assembly tends to thermally insulate the plurality of sample tubes.

58. The cover assembly of claim 33 wherein each sample tube extends for a substantial length in the flexible heating cover assembly.

59. The cover assembly of claim 33 wherein the flexible heating cover assembly is capable of withstanding thermally cycling of the samples of biological material.

60. The cover assembly of claim 33 wherein the flexible heating cover assembly helps to minimize the convective heat loss to an ambient environment.

61. A flexible heating cover assembly for an apparatus for heating samples of biological material with substantial temperature uniformity comprising:

a housing including a plurality of end caps and a plurality of side bars all composed of a thermally insulating material;

a resistive heater located within the housing, the resistive heater including at least one outer heater element area and at least one central heater element area to produce a non-uniform heat distribution along a surface exposed to a plurality of sample tubes;

a heater backing plate engaging the resistive heater to provide protection and stability to the resistive heater wherein the heater backing plate is thin and composed of a thermally conductive material;

at least one spring strip engaging a spring retainer plate, wherein the least one spring strip has a plurality of spring extensions to distribute a force uniformly over the heater backing plate; and a support plate providing sufficient stiffness to provide a reaction force for the at least one spring strip engaging the spring retainer plate with minimal deflection of the support plate, wherein the resistive heater, the heater backing plate, the spring retainer plate, and the support plate each comprise a plurality of aligned sample well openings, each sample well opening corresponding to a respective sample tube of a plurality of sample tubes.

62. The flexible heating cover assembly of claim 61 wherein the resistive heater is thin to allow rapid heating and cooling during thermal cycling of the plurality of sample tubes.

63. The flexible heating cover assembly of claim 61 wherein the at least one outer heater element area is C-shaped and located along an outer edge of a plurality of sample well openings.

64. The flexible heating cover assembly of claim 61 wherein the at least one outer heater element area includes a tapered section and curved end portions.

65. The flexible heating cover assembly of claim 61 wherein the resistive heater further comprises at least one heat carrier circuit that is not electrically connected to a heater power source wherein the at least one heat carrier circuit transfers heat through the resistive heater.

66. The flexible heating cover assembly of claim 61 wherein the resistive heater further comprises a thermistor located toward a center portion of the resistive heater to provide control of the vapor and the condensation environment of the plurality of sample tubes.

67. The flexible heating cover assembly of claim 61 wherein the resistive heater can move vertically within the flexible heating cover assembly to provide a more uniform heat distribution.

68. The flexible heating cover assembly of claim 61 wherein the heater backing plate further comprises a plurality of narrow slots to promote the flexibility of the heater backing plate and minimize the retardation of heat transfer through the heater backing plate.

69. The flexible heating cover assembly of claim 61 wherein a top surface of the heater backing plate is treated to minimize reflecting or scattering of light from the top surface of the heater backing plate.

70. The flexible heating cover assembly of claim 61 wherein the spring retainer plate retains the at least one spring strip and allows the plurality of spring extensions of the at least one spring strip to pass through the spring retainer plate.

71. The flexible heating cover assembly of claim 61 wherein the support plate retains a substantially planar shape under a loading force from the force distribution system, while the loading force acts to deform the heater backing plate attached to the resistive heater.

72. The flexible heating cover assembly of claim 61 wherein the support plate has a plurality of ribs located on a top surface of the support plate to provide stiffness to the support plate while permitting the close travel of optical scanning equipment to pass between the plurality of ribs.

73. The flexible heating cover assembly of claim 61 further comprising at least one heater slide to locate and guide the heater backing plate attached to the resistive heater in the flexible heating cover assembly.

74. The flexible heating cover assembly of claim 61 wherein at least one heater slide controls a horizontal position of the heater backing plate attached to the resistive heater, while permitting some freedom of movement in a vertical direction.

75. The flexible heating cover assembly of claim 61 further comprising an optical scanning equipment that collects optical data for quantitative PCR type experiments.

76. The flexible heating cover assembly of claim 61 wherein a plurality of mechanical interfaces transfer force between the flexible heating cover assembly and a thermal system base.

77. The flexible heating cover assembly of claim 61 wherein the flexible heating cover assembly surrounds the top and extends over at least a portion of a side of a thermal system base.

78. The flexible heating cover assembly of claim 61 wherein the flexible heating cover assembly holds the plurality of sample tubes in a plurality of sample wells of a thermal system base by imparting a substantially uniform compressive force on the plurality of sample tubes.

79. The flexible heating cover assembly of claim 61 wherein the flexible heating cover assembly tends to thermally insulate the plurality of sample tubes.

80. The flexible heating cover assembly of claim 61 wherein each sample tube extends for a substantial length in the flexible heating cover assembly.

81. The flexible heating cover assembly of claim 61 wherein the flexible heating cover assembly is capable of withstanding thermally cycling of the samples of biological material.

82. The flexible heating cover assembly of claim 61 wherein the flexible heating cover assembly helps to minimize the convective heat loss to an ambient environment.

* * * * *